United States Patent [19]
Griffin et al.

[11] Patent Number: 5,906,821
[45] Date of Patent: May 25, 1999

[54] VIRAL NUCLEOTIDE SEQUENCES

[75] Inventors: Annette Mary Griffin; Louis Joseph Norman Ross; Simon David Scott; Matthew McKinley Binns, all of Huntingdon, United Kingdom

[73] Assignee: Rhone Merieux S.A., Lyons, France

[21] Appl. No.: 08/125,039

[22] Filed: Sep. 22, 1993

Related U.S. Application Data

[63] Continuation of application No. 07/669,391, filed as application No. PCT/GB89/01075, Sep. 13, 1989, abandoned.

[30] Foreign Application Priority Data

Sep. 13, 1988 [GB] United Kingdom ................... 8821441

[51] Int. Cl.$^6$ ........................ A61K 39/255; A61K 48/00; C12N 7/01; C12N 15/86
[52] U.S. Cl. .................... 424/229.1; 424/93.2; 424/93.6; 435/235.1; 435/320.1
[58] Field of Search ................................ 435/69.1, 172.1, 435/172.3, 320.1, 235.1; 536/23.1, 23.2, 23.72; 424/229.1, 93.2, 93.6, 186.1, 191.1, 204.1, 205.1, 209.1, 215.1, 225.1, 232.1, 271.1

[56] References Cited

FOREIGN PATENT DOCUMENTS 0334530 9/1989 European Pat. Off. .

OTHER PUBLICATIONS

J. Cohen, Science, vol. 265, pp. 1371–1373, Sep. 2, 1994.
R. Jaenicke, Prog. Biophys. Molec. Biol., vol. 49, pp. 117–237, 1987.
Shih et al., PNAS, vol. 81, pp. 5867–5870, Sep. 1984.
Cranage et al., EMBO, vol. 5, No. 11, pp. 3057–3063, 1986.
Robbins et al., J. of Virol., vol. 61, No. 9, pp. 2691–2701, Sep. 1987.
Cebrian et al., PNAS, vol. 79, pp. 555–558, 1982.
Gene Sequence and Mapping Data from Marek's Disease Virus and Herpesvirus of Turkeys: Implications for Herpesvirus Classification; Buckmaster et al.; J. gen. Virol. (1988), 69, 2033–2042.
Structure and Complete Nucleotide Sequence of the Marek's Disease Herpesvirus GP57–65 Gene; Coussens, et al.; Journal of Virology, Jul. 1988, p. 2373–2379.
Identification of the Gene Encoding Marek's Disease Herpesvirus an Antigen; Isfort, et al., Journal of Virology, Aug. 1987, p. 2614–2620.
Chem. Abs. 110:149170c; J.K. Carter, et al.; U.S. Patent Application 128,836.
Genetic and Biochemical Characterization of the Thymidine Kinase Gene from Herpesvirus of Turkeys: Martin et al.; Journal of Virology, Jun. 1989, p. 2847–2852.
Rapid Indentification of Nonessential Genes of Herpes Simplex Virus Type 1 by Tn5 Mutagenesis, Weber, et al.; Science, May 1987, vol. 230, p. 576–579.
New Serotype 2 and Attenuated Serotype 1 Marek's Disease Vaccine Viruses: Comparative Efficacy; R.L. Witter; Avian Diseases 31:752–765, 1987.
Vaccination Against Marek's Disease, Ross et al.; p. 13–31.
Restriction Enzyme Map of Herpesvirus of Turkey DNA and its Collinear Releationship with Marek's Disease Virus DNA, Igariashi, et al.; Virology 157, 351–358 (1987).
"Introduction" to a poster disclosure, Apr. 1988, Herpesvirus workshop by Society for General Microbiology at Warwick University, UK, by inventior A.M. Griffin.

*Primary Examiner*—David Guzo
*Attorney, Agent, or Firm*—Larson & Taylor

[57] ABSTRACT

Various genes of herpes virus of turkeys (HVT), Marek's disease virus (MDV) and infectious laryngotracheitis (ILTV) have been identified as non-essential regions (and candidates for insertion sites for foreign genes) and/or as antigen encoding regions. The former include the HVT homologue of the HSV (herpes simplex virus) gC gene, the TK (thymidine kinase) region of MDV or ILTV, ORF3 of ILTV (as defined herein), the ribonucleotide reductase (large subunit) gene of ILTV, MDV or HVT and the ribonucleotide reductase (small subunit) gene of MDV. The antigen-encoding regions include the HVT homologues of the HSV gB, gC and gH genes, the ILTV homologue of HSV gB, ORF2 of ILTV, and the HVT homologue of the HSV-1 immediate early genes IE-175 and IE-68. Manipulation of these genes allows vaccines to be prepared comprising attenuated virus or virus carrying heterologous antigen-encoding sequences.

10 Claims, 67 Drawing Sheets

FIG 2A

```
TCGAGCTCGCCGGGATGTTTAGTCACGATAGACATCGGT
        10        20        30        40

TCGCCCAGCCGTCGAATACAGCATTATATTTAGTGTTG
        50        60        70        80

AAAATGTAGGGCTGCTTCCTCACTTAAAGGAGGAAATGGCT
        90       100       110       120

CGATTCATGTTTCATAGCAGTAGAAAACAGATTGGACCG
       130       140       150       160

TCAGTAAGTTTAGAGGGTTTTATGACTTTAGCACTATAGA
       170       180       190       200

TAATGTAACTGCGGCCCATCGCATGGCTTGGAAATATATC
       210       220       230       240

AAAGAACTGATTTTTGCAACAGCTTTATTTCTTCTGTAT
       250       260       270       280

TTAAATGTGGCGAATTGCACATCTGTCGTGCCGACAGTTT
       290       300       310       320

GCAGATCAACAGCAATGAGACTATGTATGGAAAAATGA
       330       340       350       360
```

FIG 2B

ATATATATAACATATGAAACCGAATATCCACTTATAATGA
370             380             390             400

TTCTGGGGTCAGAATCAAGCACTTCAGAAACGCAAAATAT
410             420             430             440

GACTGCAATTATTGATACAGATGTTTTTCGTTGCTTTAT
450             460             470             480

TCTATTTTGCAGTATATGGCCCCGTACGGCAGATCAGG
490             500             510             520

TGCGAGTAGAACAGATTACCAACAGCCACGCCCCATCTG
530             540             550             560

ACCCGTCCAATATTCTTGTGTCCCTGCATTTATCTCACA
570             580             590             600
                                         M  H
CAATTTATGAACAGCATCATTAAGATCATCTCACTATGCA
610             620             630             640
Y  F  R  N  C  I  F  F  L  I  V  I
CTATTTTAGGCGAATTGCATTTTTTCCTTATAGTTATT
650             660             670             680

FIG 2C

```
    L  Y  G  T  N  S  S  P  S  T  Q  N  V  T
    CTATATGGTACGAACTCATCCGAGTACCCAAAATGTGA
              690         700        710        720

S  R  E  V  V  S  S  V  Q  L  S  E  E
    CATCAAGAGAAGTTGTTTCGAGCGTCCAGTGTCTGAGGA
              730        740        750        760

E  S  T  F  Y  L  C  P  P  P  V  G  S
    AGAGTCTACGTTTTATCTTTGTCCCCACCAGTGGGTTCA
              770        780        790        800

T  V  I  R  L  E  P  P  R  K  C  P  E  P
    ACCGTGATCCGTCTAGAACCGCGGCGAAAATGTCCCGAAC
              810        820        830        840

R  K  A  T  E  W  G  E  G  I  A  I  L
    CTAGAAAAGCCACCGAGTGGGGTGAAGGAATCGCGATATTA
              850        860        870        880
```

FIG 2D

```
  F   K   E   N   I   S   P   Y   K   F   K   V   T
TTTAAAGAGAATATCAGTCCATATAAATTTAAAGTGACGC
|||||||||||||||||||||||||||||||||||||||
GAGAATATCAGTCCGTATAAATTCAAAGTAACAC
    890       900       910       920

L   Y   Y   K   N   I   I   Q   T   T   T   W   T   G
TTTATTATAAAAATATCATTCAGACGACGACATGGACGG
|||||||||||||||||||||||||||||||||||||||
TTTACTATAAGAACGTTATACAAACTACGACGTGGACTG
    930       940       950       960

T   T   Y   R   Q   I   T   N   R   Y   T   D   R
GGACGACATATAGACAGATCACTAATCGATATACAGATAG
|||||||||||||||||||||||||||||||||||||||
GGACGACGTACAGACAGATAACTAACAGGTATACAGATAG
    970       980       990      1000
```

FIG 2E

```
        ---------------D-----------------
  T  P  V  S  I  E  E  I  T  D  L  I  D
GACGCCCGTTTCCATTGAAGAGATCACGGATCTAATCGAC
   ||||||||||||||||||||||||||||||||||||
AACACCCGTGTCTATCGACGAAATTACTGATTGATAGAT
         1010      1020      1030      1040

-------K------------
  G  K  G  R  C  S  S  K  A  R  Y  L  R  N
GGCAAAGGAAGATGCTCATCTAAAGCAAGATACCTTAGAA
   ||||||||||||||||||||||||||||||||||||
GGTAAGGGGAAATGTTCATCCAAAGCCCGTATCTTCG
       1050      1060      1070      1080

N  V  Y  V  E  A  F  D  R  D  A  G  E
ACAATGTATATGTTGAAGGCGTTTGACAGGATGCGGGAGAA
         1090      1100      1110      1120

K  Q  V  L  L  K  P  S  K  F  N  T  P
AAACAAGTACTTCTAAAACCATCAAAATTCAACACGCCC
         1130      1140      1150      1160
```

FIG 2F

```
    E  S  R  A  W  H  T  T  N  E  T  Y  T  V
   GAATCTAGGGCATGGCACGACTAATGAGACGTATACCG
   |||||||| |||||| || ||||||| |||| ||||
   GGCATGGCATACGACCAACGAGACGTACACCG
   1170      1180      1190      1200

W  G  S  P  W  I  Y  R  T  G  T  S  V
   TGTGGGATCACCATGGATATCGAACGGAACCTCCGT
   ||||||||| ||||||| |||| |||||| ||||||
   TGTGGGGATCTCCATGGTATATAGAACGGGCACGTCCGT
   1210      1220      1230      1240

——A——
    N  C  I  V  E  E  M  D  A  R  S  V  F
   CAATTGTATAGTAGAAGAAATGGATGCCCGCTCTGTGTTT
   ||| || || ||||||| |||||||| |||| ||| |||
   CAACTGCATAGTAGAAGAAGATGGATGCCAGATCAGCATTT
   1250      1260      1270      1280
```

FIG 2G

```
       ——T——
    P  Y  S  Y  F  A  M  A  N  G  D  I  A  N
    CCGTATTCATATTTGCAATGGCCAATGGCGACATCGCGA
    ||| ||  || ||||||||||||||| || |||| ||||
    CCATACACGTACTTTGCAATGGCCAATGGAGATATCGCAA
          1290        1300        1310        1320

——M——           ——T——T——D——
    I  S  P  F  Y  G  L  S  P  P  E  A  A
    ACATATCTCCATTTTATGGTCTATCCCACCAGAGGCTGC
    |||| |||||||||||| ||||  |  |||  ||||| ||
    ACATGTCTCCATTTTATGAACAACTCCAACGACGCGGC
          1330        1340        1350        1360

——S——              ——R——R——
    A  E  P  M  G  Y  P  Q  D  N  F  K  Q
    CGGAGAACCCATGGGATATCCCCAGGATAATTCAAACAA
    ||| || |||||| |||| |||| |||||| |||  |||
    CGGGGAGCCCATGAGCTATCCGCAAGACGATTCAGGCAA
          1370        1380        1390        1400
```

FIG 2H

```
    -F————————————P————————————T————
     L  D  S  Y  F  S  M  D  L  D  K  R  R  K
    CTAGATAGCTATTTTCAATGGATTTGGACAAGGTCGAA
    ||| ||||||| — |||||||||| ||| |||| ||||
    TTTGACAGCTATTTCCCATGGATTTGGATACGCGCCGAA
         1410       1420       1430       1440

—|
     A  S  L  P  V  K  R  N  F  L  I  T  S
    AAGCAAGCCTCCAGTCAAGGTAACTTTCTCATCACATC
    ||
    AA
            1450       1460       1470       1480

H  F  T  V  G  W  D  W  A  P  K  T  T
    ACACTTCACAGTTGGGTGGGACTGGGCTCCAAAAACTACT
            1490       1500       1510       1520

R  V  C  S  M  T  K  W  K  E  V  T  E  M
    CGTGTAGTTCAATGACTAAGTGGAAAGAGGTGACTGAAA
            1530       1540       1550       1560

L  R  A  T  V  N  G  R  Y  R  F  M  A
    TGTTGCGTGCAACAGTTAATGGAGATACAGATTTATGGC
            1570       1580       1590       1600
```

FIG 2I

```
  R   E   L   S   A   T   F   I   S   N   T   T   E
CCGTGAACTTTCGGCAACGTTTATCAGTAATACGACTGAG
      1610        1620        1630        1640

F   D   P   N   R   I   I   L   G   Q   C   I   K   R
TTTGATCCAAATCGCATCATATTAGGACAATGTATTAAAC
      1650        1660        1670        1680

E   A   E   A   A   I   E   Q   I   F   R   T   K
GCGAGGCAGAAGCAGCAATCGAGCAGATATATTAGGACAAA
      1690        1700        1710        1720

Y   N   D   S   H   V   K   V   G   H   V   Q   Y
ATATAATGACAGTCACGTCAAGGTTGGACATGTACAATA
      1730        1740        1750        1760

F   L   A   L   G   G   F   I   V   A   Y   Q   P   V
TTTCTTGGCTCTCGGGGATTTATTGTAGCATATCAGCCTG
      1770        1780        1790        1800

L   S   K   S   L   A   H   M   Y   L   R   E   L
TTCTATCCAAATCCCTGGCTCATATGTACCTCAGAGAATT
      1810        1820        1830        1840
```

FIG 2J

```
         M  R  D  N  R  T  D  E  M  L  D  L  V
        GATGAGAGACAACAGGACCGATGAGATGCTCGACCTGGTA
              1850       1860       1870       1880

N  N  K  H  A  I  Y  K  K  N  A  T  S  L
AACAATAAGCATGCAATTTATAAGAAAAATGCTACCTCAT
      1890       1900       1910       1920

S  R  L  R  R  D  I  R  N  A  P  N  R
        TGTCACGATTGCGGCGAGATATTCGAAATGCACCAAATAG
              1930       1940       1950       1960

K  I  T  L  D  D  T  T  A  I  K  S  T
AAAAATAACATTAGACGACACCACAGCTATTAAATCGACA
      1970       1980       1990       2000

S  S  V  Q  F  A  M  L  Q  F  L  Y  D  H
        TCGTCTGTTCAATTCGCCATGCTCCAATTCTTTATGATC
              2010       2020       2030       2040

I  Q  T  H  I  N  D  M  F  S  R  I  A
ATATACAAACCCATATTAATGATATGTTTAGTAGGATTGC
      2050       2060       2070       2080
```

FIG 2K

```
        T  A  W  C  E  L  Q  N  R  E  L  V  L
        CACAGCTTGGTGTGCGAATTGCAGAATAGAGAACTTGTTTA
              2090      2100      2110      2120

W  H  E  G  I  K  I  N  P  S  A  T  A  S
        TGGCACGAAGGGATAAAGATAAATCCTAGCGCTACAGCGA
              2130      2140      2150      2160

┌─────────────────
                               A  T  L  G  R  R  R  V  A  A  K  M  L  G
                               GTGCAACATTAGGAAGGAGAGTGGCTGCAAAGATGTTGGG
                                                                  ║║ ║║║║║║║║║║║║
                                                                  GCCAAAATGTTGGG
                                    2170      2180      2190      2200

──────D─────────────────────────I──E──T─────S─
  D  V  A  A  V  S  S  C  T  A  I  D  A
GGATGTCGCTGCTGTATCGAGCTGCACTGCTATAGATGCG
║║║║║║ ║║║║║ ║║║║ ║║ ║║║ ║║║ ║║║║║║║║║║║║
TGACGATGCCGCGTATCATCATGTATTGAGACTGATTCA
      2210      2220      2230      2240
```

FIG 2L

```
     -D                                              V
      E  S  V  T  L  Q  N  S  M  R  V  I  T  S
     GAATCCGTCACTTTGCAAAATTCTATGCGAGTTATCACAT
     ||  ||  || ||  |||| ||||||||  ||| |||  |||| ||
     GATTCTGTTACCTTACAAAATTCCATGCGGTTGTCACCT
            2250      2260       2270      2280

T  N  T  C  Y  S  R  P  L  V  L  F  S
     CCACTAATACATGTTATAGCCGACCATTGGTTCTATTTC
     || |||||||| || ||  ||||||||  || || ||||||||||
     CTACCAATACTTGTTATAGCCGCCCTTTAGTGTTATTCTC
           2290       2300      2310      2320

-D---R---D--K
      Y  G  E  N  Q  G  N  I  Q  G  Q  L  G
     ATATGGAGAAACCAAGGAAACATACAGGAGAACTCGGTG
     ||  ||||||  |||| |||  ||| ||  ||||  |||| ||
     CTACGGGACCGACACGACAAGGACAAGGACAGTTGGGGG
           2330      2340       2350      2360
```

FIG 2M

```
                 I                                                I
    E   N   N   E   L   L   P   T   L   E   A   V   E   P
    AAAACAACGAGTTGCTTCCAACGCTAGAGGCTGTAGAGC
    ||||||  ||  |||  ||||||  ||||||||  ||||||
    AAAACAAATGAATTGATTCCAACTCTAGAGGCCATAGAGC
              2370          2380          2390          2400

C   S   A   N   H   R   R   Y   F   L   F   G   S
    CATGCTCGGCTAATCATCGTAGATATTTCTGTTGGATC
    |||  ||||  ||||||  ||||||||||  |||||||
    CATGTTCGGCCAATCATCGTAGA
              2410          2420          2430          2440

G   Y   A   L   F   E   N   Y   N   F   V   K   M
    CGGTTATGCTTTATTTGAAAACTATAATTTTGTTAAGATGG
              2450          2460          2470          2480

V   D   A   A   D   I   Q   I   A   S   T   F   V   E
    TAGACGCTGCCGATATACAGATTGCTAGCACATTTGTCG
              2490          2500          2510          2520
```

FIG 2N

```
  L   N   L   T   L   L   E   D   R   E   I   L   P
AGCTTAATCTAACCCTGCTAGAAGATCGGAAATTTGCC
          2530      2540      2550      2560

L   S   V   Y   T   K   E   E   L   R   D   V   G
TTTATCCGTTTACACAAAGAAGAGTTGCGTGATGTTGGT
     2570      2580      2590      2600

V   L   D   Y   A   E   V   A   R   R   N   Q   L   H
GTATTGGATTATGCAGAAGTAGCTCGCCGCAATCAACTAC
     2610      2620      2630      2640

E   L   K   F   Y   D   I   N   K   V   I   E   V
ATGAACTTAAATTTTATGACATAAACAAAGTAATAGAAGT
      2650      2660      2670      2680

D   T   N   Y   A   F   M   N   G   L   A   E   L
GGATACAAATTACGCGTTTATGAACGGTTTGGCCGAATTG
      2690      2700      2710      2720

F   N   G   M   G   Q   V   G   Q   A   I   G   K   V
TTTAACGGTATGGGTCAGTAGGCAAGCTATAGGCAAAG
      2730      2740      2750      2760
```

FIG 2ϕ

```
  V  V  G  A  A  G  A  I  V  S  T  I  S
TTGTAGTAGGGGCTGCCGGTGCAATCGTATCTACCATATC
      2770        2780        2790        2800

G  V  S  A  F  M  S  I  P  L  G  L  S
TGGTGTCTCTGCTTTCATGTCAATCCCTTTGGGCTTTCG
      2810        2820        2830        2840

A  I  G  L  I  I  I  A  G  L  V  A  A  F
GCAATCGGTTTAATCATTATAGCAGGACTCGTGGCTGCAT
      2850        2860        2870        2880

L  A  Y  R  Y  V  N  K  L  K  S  N  P
TTTTAGCATATCGTTATGTAAACAAGCTTAAAAGCAATCC
      2890        2900        2910        2920

M  K  A  L  Y  P  M  T  T  E  V  L  K
AATGAAAGCCCTTTATCCTATGACAACAGAAGTGCTTAAG
      2930        2940        2950        2960

A  Q  A  T  R  E  L  H  G  E  E  S  D  D
GCACAGGCAACGCGGAGTTGCATGGCGAGGAATCAGATG
      2970        2980        2990        3000
```

FIG 2P

```
      L   E   R   T   S   I   D   E   R   K   L   E   E
ATTTGGAACGAACATCTATTGATGAAAGAAAATTAGAAGA
      3010        3020        3030        3040

A   R   E   M   I   K   Y   M   A   L   V   S   A
AGCTAGAGAAATGATAAAATATGGCGTTAGTCTCCGCG
      3050        3060        3070        3080

E   E   R   H   E   K   K   L   R   R   K   R   G
GAAGAACGCCACGAGAAAAAACTGCGGAGAAAGAGGCGAG
      3090        3100        3110        3120

T   T   A   V   L   S   D   H   L   A   K   M   R
GCACTACCGCCGTTCTATCGGACCACCTGGCAAAAATGAG
      3130        3140        3150        3160

I   K   N   S   N   P   K   Y   D   K   L   P   T
GATTAAAAATAGTAACCCTAAATATGATAAGTTACCTACT
      3170        3180        3190        3200

T   Y   S   D   S   E   D   D   A   V   *
ACATATTCAGACTCAGAAGATGATGCTGTGTAAGTGGGCA
      3210        3220        3230        3240

CTATTATATTTGAACTGAATAAAACGCATAGAGCATGATA
      3250        3260        3270        3280
```

FIG 2Q

TGGTTTACTCATTATTGCGAGATATAAAGCATATTCAAT
3290        3300        3310        3320

ACGATATATTGCGAACGTGATGCTAAAAACATAGCTCCCT
3330        3340        3350        3360

GTATTATTGATGCGCCATCATTTGATTAATAAATACATCG
3370        3380        3390        3400

ACGCCGGCATCACTGGTGCGGTGTATACCAGCTACGGCGC
3410        3420        3430        3440

TAGCATTCATGGTATCCCGTGATTGCTCGATGCTTTCCTT
3450        3460        3470        3480

CTGAATTCCGTCGGAACGCTCCTGAGAGATGGTCGCAGTT
3490        3500        3510        3520

ATTGGTACATTTCGACCAGCCTCCGGATCTGAAACTGGCA
3530        3540        3550        3560

CAGGAATGCACCGTGGAATTGGTAGAAGTTTTTCCTTCCG
3570        3580        3590        3600

FIG 2R

TGGAAGGCATAGGCGTTCGACTCCCATGGGCCATGAAACTGTGGGATGT
3610           3620          3630          3640          3650

FIG 4A

TATTATTGGTCCATGCTAGAATAGTCATACGCTACGATCT
          10        20        30        40

GTTGCTATATATGACTATCGCCAAACTGTTAAACCCGCGA
          50        60        70        80

AGAATATATTTCATATATAAACCTAAGGGCCCCTCAGTCTGA
          90       100       110       120
                                   M  K  F  Y  C  L

TTTTTTGTGAAAACGTGTATACCATGAAGTTTTACTGCCT
         130       140       150       160
 I  R  F  M  I  I  A  N  L  Y  S  S  Y

AATCCGTTTCATGATCATAGCCAATCTTTATTCATCTTAC
         170       180       190       200
 Q  I  S  L  P  G  T  Y  P  S  Q  I  L  L

CAAATATCGCTTCCAGGCACATATCCATCGCAAATATTGC
         210       220       230       240
 D  M  K  N  S  P  L  V  R  F  N  I  S

TTGACATGAAGAACTCGCCGCTCGTACGCTTTAATATATC
         250       260       270       280

FIG 4B

```
T  R  D  Y  K  D  E  T  L  W  I  R  K
GACGCGTGATTATAAAGACGAGACACTCTGGATACGAAA
            290         300         310         320

N  S  T  F  V  Y  I  D  T  A  V  T  T  A
AATTCGACATTTGTTTATATCGATACGGCTGTGACGACAG
            330         340         350         360

N  V  I  F  Y  L  P  I  G  Q  V  R  Q
CGAACGTTATCTTTTATCTGCCGATCGGTCAGGTACGACA
            370         380         390         400

M  V  F  F  K  R  P  I  S  R  L  L  T
AATGGTTTTTTTCAAGCGTCCAATATCCAGGCTACTAACG
            410         420         430         440

S  N  N  L  V  K  F  I  N  T  G  S  Y  A
TCCAATAACCTGGTTAAATTTATTAATACCGGTTCATACG
            450         460         470         480

N  H  F  K  T  E  L  S  P  Y  L  S
CCAATCATACATTCAAGACAGAACTTTCACCCTATTTGTC
            490         500         510         520
```

FIG 4C

```
       K   T   N   T   P   L   K   K   Y   E   I   V   V
       GAAAACCAATACACCCGTTGAAGAAATATGAAATTGTTGTC
                 530         540         550         560

D   Q   P   T   G   E   N   P   P   A   G   F   G   S
       GATCAACCTACTGGAGAAAACCCTCCGGCAGGGTTCGGAA
                 570         580         590         600

L   K   P   A   D   F   L   N   P   G   Y   K   F
       GTTTAAAACCGGGCAGACTTTCTCAACCCCGGATACAAGTT
                 610         620         630         640

V   L   T   S   E   L   V   G   A   Y   T   K   R
       CGTTCTCACAAGCGAGTTGGTAGGAGCCTACACAAAACGA
                 650         660         670         680

S   C   F   V   D   P   M   D   S   L   V   P   I   D
       TCTTGTTTTGTCGATCCGATGGATTCTCTCGTCCCGATAG
                 690         700         710         720

Y   D   H   V   R   T   I   I   F   G   S   A   G
       ATTATGATCATGTACGAACCATTATATTCGGATCTGCTGG
                 730         740         750         760
```

FIG 4D

```
      M  E  I  L  K  M  G  I  T  L  A  S
GATGGAGATTTAATGAAGATGGGAATTACTTTGGCATCT
             770          780          790          800

M  T  I  S  T  K  Y  N  P  P  I  E  L  I
ATGACCATTTCGACGAAATATAATCCTCCTATTGAACTGA
        810          820          830          840

I  S  A  K  Y  R  N  L  S  L  L  W  P
TAATATCTGCAAAGTACCGAAATTTATCACTGTTGTGGCC
        850          860          870          880

P  R  Q  Q  Y  E  P  V  N  K  G  T  G
ACCCCGACAACAATATGAACCTGTAAATAAAGGGACTGGA
        890          900          910          920

R  P  H  W  I  Y  L  L  G  V  Y  R  N  V
CGCCCCCATTGGATCTACCTATTAGGTGTGTATAGAAACG
        930          940          950          960

S  D  S  E  R  D  S  Y  M  N  M  I  K
TTTCGGACTCCGAGCGTGACTCATACATGAATATGATTAA
        970          980          990          1000
```

FIG 4E

```
  S   L   G   D   S   M   D   Y   H   F   L   I   S
GAGTCTGGGGCGGATTCTATGGATTATCACTTCCTAATTAGC
            1010           1020           1030           1040

R   A   H   A   Q   M   L   I   L   A   A   E   D   R
AGAGCGCATGCCCAGATGCTGATACTGGCAGCAGAGGACC
            1050           1060           1070           1080

L   V   D   E   M   H   S   F   R   N   V   I   A
GGCTCGTGGATGAAATGCATAGTTTCAGGAACGTTATTGC
            1090           1100           1110           1120

R   L   F   V   S   L   F   A   F   I   R   N   A
GCGTTTATTTGTATCGTTGTTCGCATTCATACGTAACGCA
            1130           1140           1150           1160

F   Q   S   G   Y   T   S   L   N   D   I   E   I
TTTCAGTCTGGCTACACCTCTCTTAATGACATAATTGAAA
            1170           1180           1190           1200

E   A   D   L   R   L   I   V   E   G   I   S   S
TCGAAGCCGATTTGAGGTTAATTGTAGAAGGCATTTCTTC
            1210           1220           1230           1240
```

FIG 4F

```
   A   A   F   R   K   D   A   S   T   H   F   L   I
TGCTGCATTTCGTAAAGACGCTAGTACACACTTTCTTATA
       1250          1260          1270          1280

S   G   T   P   I   K   D   S   K   A   D   L   I   K
TCGGGAACGCCCATAAAAGATAGCAAAGCGGATTTAATTA
       1290          1300          1310          1320

S   L   L   S   K   V   I   R   P   I   S   G   H
AATCGTTGTTGTCTAAAGTCATTCGACCAATTTCCGGACA
       1330          1340          1350          1360

T   R   P   L   S   A   I   Q   H   L   F   L   L
TACACGTCCCTTATCTGCGATACAACATCTATTCCTTTTG
       1370          1380          1390          1400

R   S   A   Y   A   L   D   I   P   R   Q   N   G   S
AGATCCGCTTATGCATTGGATATACCCCGTCAAAACGGAT
       1410          1420          1430          1440

L   S   E   Q   V   S   T   V   A   L   S   F   I
CTTTGAGCGAACAGGTATCTACAGTGGCACTGTCGTTCAT
       1450          1460          1470          1480
```

FIG 4G

```
  E   N   I   H   S   E   A   M   R   D   I   L   S
TGAAATATTCACAGCGAGGCCATGAGGGACATTCTGTCA
      1490        1500       1510       1520

W   N   T   T   K   H   A   L   Y   Y   A   F   A
TGGAACACTACAACAAAGCATGCGTTGTATTATGCATTCG
      1530        1540       1550       1560

S   I   L   Q   R   P   L   T   E   W   G   A   S
CGAGTATTTTGCAACGGCCACTGACCGAATGGGGCGCCTC
      1570        1580       1590       1600

R   N   A   R   R   A   I   L   L   A   S   S   M
AAGAAATGCACGGAGGGCAATACTATTAGCATCATCGATG
      1610        1620       1630       1640

C   T   E   E   H   V   I   A   T   E   L   A   I   Q
TGTACAGAAGAGCATGTTATCGCAACTGAGTTGGCTATTC
      1650        1660       1670       1680

E   L   Y   V   K   I   R   S   N   A   D   P   I
AAGAACTGTATGTCAAAATCAGAGAAGTAATGCCGACCCAAT
      1690        1700       1710       1720
```

FIG 4H

```
  H   L   L   D   V   Y   T   P   C   L   S   S   L
ACACCTTCTAGACGTATATACACCATGTCTTTCTTCACTA
             1730          1740          1750          1760

R   L   D   L   S   E   H   H   R   I   Y   A   M   A
CGATTGGACCTTTCCGAACACCATCGGATATACGCAATGG
     1770          1780          1790          1800

D   V   V   F   Y   P   D   I   Q   Q   Y   L   K
CAGATGTAGTTTTCTATCCAGACATTCAGCAGTATTTGAA
     1810          1820          1830          1840

K   K   S   H   E   G   N   M   K   E   D   D   L
AAAAAAATCCCATGAGGGTAATATGAAGGAAGATGATCTC
     1850          1860          1870          1880

E   T   K   A   E   Y   I   L   T   K   L
GAAACAAAGGCGGAATACATCCTCACCAAGCTT
     1890          1900          1910
```

FIG 5A

```
AAGCTTTTTGTAAAAACGATTATGACCACGGACACCCGCT
         10        20        30       40

TTTAGCAATCCTGCCATAAGGTGGTTCCCGCGTGCTTGC
         50        60        70       80

CTCGAAGACACAATTGCCAGCTAATCCAGCATTACCATATATT
         90       100       110      120

|——S—Q
                             M  A  L  P
CCTTGGCTTGCATTTGGATCTGCGCGTCGATGGCATTGCC
                            |||||||
                            ATGGCATCTCA
        130       140       150      160

|—M—T—S—A—Q—I
 R  R  P  P  T  L  T  R  V  Y  L  D  G
GAGAAGACCGGCCCACGTTAACGCGAGTTTATCTAGACGGA
||  ||  ||     ||  ||  ||  ||  ||  ||  ||
GATGACATCTGCACAGCTCATACGTGTATACCTCGATGGA
        170       180       190      200
```

FIG 5B

```
        -S---M-----------------M----------E---I----
         P  F  G  I  G  K  T  S  I  L  N  A  M  P
         CCGTTTGGTATAGGCAAAACGTCTATACTAAACGCTATGC
         — |||||| ||||||| || — ||| — || ||
         TCAATGGGTATAGGTAAAACGTCAATGTTGAATGAGATAC
             210        220        230        240

----T------L|                               
         D  H  T  P  D  G  A  P  I  L  K  V  Y
         CCGACCACACGCCCGATGGGCTCCTATATTGAAAGTGTA
         — ||
         CGACGCCATCTT
             250        260        270        280

E  P  M  K  Y  W  R  C  Q  S  T  D  L
         CGAACCAATGAAATATTGGAGATGCCAGTCTACCGATTTG
             290        300        310        320
```

FIG 5C

```
         ———————————————R———
    V V A A N E T P E R R R G G
    GTGGTAGCTGCCAACGAAACGCCAGAACGTAGGCGTGGTG
              |||  ||  |||
                        ATCGTCGTCGCAGGG
    330       340       350       360

——E——F——L—————————S————V——T——A
    A L S G F Q S D M I M A S
    GAGCTTTATCACGATTCCAATCTGACATGATCATGGCATC
    |||  ||   |||  |||||  ||||||   ||| ||
    GAGAGTTTTCTTTATTCAATCTAGCATGATTGTAACAGC
    370       380       390       400

——L——S——K—————————————V————
    I Q A R F A D P Y L L F H
    TATACAAGCCAGATTTGCCGATCCATATTGCTTTTTCAC
    ||||| |||  ||||| ||||  |||  |  | |||
    TTTACAATCAAAGTTTGCAGATCCCTATCTGTATTTCAT
    410       420       430       440
```

FIG 5D

```
---H---R---I---T---G---T---R
---E---R---L---S---S---K---C---R---G---K---I---E---I---C
GAACGGTTATCATCTAAAATGTAGAGGAAAAATAGAAATAT
  ||  ||||||  ||  ||||  ||  ||||||  ||||||
GAGCGCTTATCGTCGAAGTGTCATCGCATAACAGGAACAC
              450           460           470           480

---G---N---S---L---I---A---H---P
---D---T---P---A---I---I---L---M---L---D---R---H---P
GCGATACTCCAGCAATTATATATTAATGCTGGATAGGCACCC
 ||  ||||  ||||||  |||||||||  ||  ||  ||
GTGGCAATCCATCGCTTATATTAATTCTAGATCGACATCC
       490           500           510           520

---I---S---T---V---A---H---
---V---A---A---I---L---C---F---P---I---T---R---Y---L
TGTGGCGGCGATATATGTTCCAATCACTCGCTATTTA
||  ||  ||||  ||||  |||||  ||  |||||
CATATCCGCTACCGTATGTTTCCCATTGCTCGACATTTA
       530           540           550           560
```

FIG 5E

```
-T----D---C----------M-----------
 L  G  E  Y  S  L  E  M  L  I  S  S  I  I
CTTGGAGAATATTCTTTGGAAATGTTGATTAGCTCTATAA
|||||||||| ||  |||| |||| |||||||  ||||||
ACTGGAGATTGTTCCTTGAGATGCTAATTAGTATGATAA
         570       580       590       600

--------------Q----P---------V--I-
 R  L  P  L  E  S  P  G  C  N  L  T  V
TAAGACTTCCGTTGAATCCCCGGATCAACCTGACAGT
|||| || || ||||  |||| |||||||||  ||||
TAAGGTTGCCCCAGGAACCGCCAGGATGCAACTTGGTGAT
         610       620       630       640

--V--D----H----------S----L-
 T  I  L  P  D  E  K  E  H  V  N  R  I
CACAATCCTTCCCGACGAAAAGGAACACGTTAATAGGATT
|||  |||||||| ||||||||| ||| ||||||  ||||
TGTCGATCTACATGACGAAAAGGAGCATGTTAGCCGTCTA
         650       660       670       680
```

FIG 5F

```
     S            N           T            K    T       L    L
     C  S  R  D  R  P  G  E  T  A  D  R  N  M
     TGTTCAAGAGATAGACCGGGTGAAACGGCAGATAGAAATA
     ||||  ||||  |||  ||||  ||||  |||  |||||  |
     TCTTCACGGAATAGGACCGGCGGGCGAGAAAACAGATCTACTAA
                690         700         710         720

A                    S—C
     L  R  T  L  N  A  V  Y  A  S  L  V  D
     TGCTCAGAACACTCAATGCCGTATACGCCATCTTTGGTGGA
     ||||||  |||  ||  ||||  ||  |||||||||||  ||
     TGCTCAGGGCACTTAATGCAGTGTATTCCTGTTTAGTAGA
                730         740         750         760

I—M           H—I       S
     T  V  K  Y  A  N  L  T  C  P  Y  E  K
     CACGGTTAAATACGCAAATCTAACATGCCCTTACGAGAAA
     |||  |||  ||||||||||  |||||  ||  |||||
     CACTATTATGTACGCAAATCATATTGTCCTACAGTAAG
                770         780         790         800
```

FIG 5G

```
   D    E         S         D                      D
   E    S    W    E    M    E    W    L    G    L    P    W    F    E
GAAAGCTGGGAAATGGAATGGTTGGACTTCCCTGGTTTG
||||| |||||||| |||||||| || |||||||
GATGAATGGAATCTGAATGGTTGATCTACCATGGTTTG
        810            820            830            840

T         A    T         N    E              T
   E    S    L    L    E    E    F    I    S    R    P    R    P
AAGAGTCATTACTTGAAGAATTCATCTCGGCCCCCGCCC
 ||||| ||| ||   ||||    ||| |  | |||
ATACATCTTTGCCACAACGTTTATAAACGAACCTCGTAC
        850            860            870            880

...D    Y    R    G    S         V    S         H    H
   V    I    C    S    R    T    R    M    P    L    D    R    T
TGTTATTTGTTCGAGAACTCGAATGCCGCTGGACCGAACT
||   || ||| ||  |||  | ||||| ||  ||||||
TG...ATTATCGCGGTAGTAGGGTGTCATTACACCATACG
        890            900            910            920
```

FIG 5H

```
             |————————R————————|
     L  L  A  I  F  K  R  K  E  L  C  S  E  N
     CTCCTGGCCATTTTAAACGGAAAGAGCTGTGTAGCGAAA
     ||  ||  ||  ||||||  |||  ||     ||
     CTTTTAGGCGATATTTAAGGCGGAGAATTATGT
           930       940       950       960

G  E  L  L  T  Q  Y  S  W  I  L  W  G
     ATGGGGAGCTGTTAACTCAGTATTCTTGGATATTGTGGGG
           970       980       990      1000

L  L  T  K  L  H  T  I  N  V  E  L  F
     ATTACTGACTAAACTACACACCATTAATGTCGAATTATTT
          1010      1020      1030      1040

|———V—E—L—L
     D  I  S  G  M  S  R  R  E  C  A  S  A  I
     GACATTAGCGGTATGTCACGTCGAGAATGCGCCAGCGCTA
                                 ||
                                 TGTGTAGAACTGC
          1050      1060      1070      1080
```

FIG 5I

```
----D----    ----S----        ----V----    ----H--S----
  M H T M P E R L S T L A S
TAATGCATACTATGCCGGAGAGATTGTCTACTCTCGCTAG
|||  |||||| ||||||| |||||||   ||||| |||
TTATGGATACTATGTCGGAGAGATTGGTAACACATAGTAG
    1090         1100       1110       1120

----A--F----   ----I----  ----A---- ----L--A----
  W N D L C E L E D D V I S
CTGGAATGATGATTTATGCCGAGCTTGAAGATGATGTAATTCC
||||||||| |  ||| |||  |||||||| |||  |||| ||
CTGGAATGATGCCCTTCGAGATTGAAGCTGATGATGTACTAGCC
      1130      1140      1150       1160

----E----  ----A--M--*----|
  Y N K G M C N E V G A S R *
TATAATAAGGAATGTGTAACGAGGTTGGAGCGTCTCGAT
|||||||| ||  ||| ||   ||| |||||  |||||
TATAATAAAGAGATGGCTATGTAA
     1170       1180       1190      1200

AATTCTTCTTAATCTGCTGGTATTGTTACTGCCATAACT
       1210       1220      1230       1240
```

FIG 5J

TATTATTGGTCCATGCTAGAATAGTCATACGCTACGATCT
1250              1260              1270              1280

GTTGCTATATATGACTATCGCCAAACTGTTAAACCCGGCGA
1290              1300              1310              1320

AGAATATATTTCATATAAACCTAAGGGCCCCCTCAGTCTGA
1330              1340              1350              1360

TTTTTGTGAAAACGTGTATACCA
1370              1380

FIG 6A

```
  1 CAGCTGCCTATGTAGTGAAATCTATACTGGGATTT
    ATCATAACTAGTTTACTTGTTTGTATATTAGTAGCGCTATCT
    TGACCAAATCGTTGTTCACATCTGGCCATATACGTATTGATC
121 GTTGTTTCGAACCGGAATAAACTTTCATACATAC
    TAAACGATGAGTTGTGTTTATGAGCGTTGAAAACAAGGT
    ACCATCGGTTTAAAACTAAGTTGCATATCGTAATCCACAAAA
                                    M L T P R V
241 ATCATTTTATACATCATCCCGAAGAGACACCAAACG
    TAACCCTCTACATATCTTCCCTCATGCTCACGCCGCGTGT
    L R A L G W T G L F F L L L S
    TACGAGCTTTGGGGTGGACTGGACTCTTTTTTTGCTTTTAT
              P S N V L G A S L S R
361 CTCCGAGCAACGTCCTAGGAGCCAGCCTTAGCCGG
    D L E T P P F L S F D P S
    GATCTCGAAACACCCCATTTCTATCCTTTGATCCATCCA
```

FIG 6B

```
    N I S I N G A P L T E V P H A P
    ACATTCAATTAACGGCGGCCTTTAACTGAGTACCTCATGCAC
                 S T E S V S T N S E S T
481 CTTCCACAGAAAGTGTCAACAAATTCGAAAGTACC
    N E H T I E T T G K N A Y
    AATGAACATACCATAACAGAAACGACGGGCAAGAACGCATACA
    I H N N A S T D K Q N A N D
    TCCACAACAATGCGTCTACGGACAAGACAAAAATGCGAACG
                 T H K T P N I L C D T E
601 ACACTCATAAACGCCCAATATACTCTGCGATACGGA
    E V F V F L N E T G R F V C
    AGAAGTTTTTGTTTTCCTTAACGAAACGGGAAGATTTGTTTGT
    T L K V D P P S D S E W S N
    ACTCTCAAAGTCGACCCCCCTCGATAGTGAATGGTCCA
                 F V L D L I F N P I E Y
721 ACTTTGTTCTAGATCTTGATCTTTAACCAATTGAATA
    H A N E K N V E A A R I A G
    CCACGCCAACGAAAAGAATGTGGAAGCGGCCGTATCGCTGGT
```

FIG 6C

```
      L Y G V P G S D Y A Y P R Q
     CTCTATGGAGTCCCCGGATCAGACTATGCATACCCACGTC
                   S  E  L  I  S  S  I  R  R  D  P
841 AATCTGAATTAATTCTTCGATTCGACGAGATCCCC
 Q  G  T  F  W  T  S  P  S  P  H  G  N  K
AGGGCACATTTTGGACGAGCCCATCACCTCATGAAACAA
      Y F I W I N K T T N T M G V E
     GTACTTCATATGGATAAACAAACCAATACGATGGGCGTGG
                   I  R  N  V  D  Y  A  D  N  G  Y
961 AAATTAGAAATGTAGATTATGCTGATAATGGCTAC
 M  Q  V  I  M  R  D  H  F  N  R  P  L
ATGCAAGTCATTATGCGTGACCATTTTAATCGGCCTTTAA
      I D K H I Y I R V C Q R P A S V
     TAGATAAACATATTTACATACGTGTGTCAACGACCTGCATCAG
                   D  V  L  A  P  P  V  L  S  G  E  N
1081 TGGATGTACTGGCCCCTCCAGTCCTCAGGGGAGAAAA
 Y  K  A  S  C  I  V  R  H  F  Y  P  P  G
TTACAAGGCATCTTGTATCGTTAGACACTTTTATCCCCCTGGA
```

FIG 6D

```
     S  V  V  Y  S  W  R  Q  N  G  N  I  A  T
     TCTGTCTATGTATCTTGGAGACAGAATGAAACATTGCAA

P  R  K  D  R  D  G  S  F  W  W  F
1201 CTCCTCGGAAAGATCGCGATGGAAGTTTTGGTGTT

E  S  G  R  G  A  T  L  V  S  T  I  T  L
     CGAATCTGGTAGAGGAGCTACGTTGGTTTCTACAATAACATTG

G  N  S  G  I  D  F  P  P  K  I  S  C  L
     GGAAATTCAGGAATTGATTCCCCCCAAAATATCTTGTC

V  A  W  K  Q  G  D  M  I  S  T  T
1321 TGGTTGCCTGGAAGCAGGGTGATGATCAGCACGAC

N  A  T  A  I  P  T  V  Y  H  H  P  R  L
     GAATGCCACAGCTATCCCGACGGTATATCATCCCCGTTTA

S  L  A  F  K  D  G  Y  A  I  C  T  I  E
     TCCCTCGGCTTTTAAAGATGGGTATGCAATATGTACTATAG

C  V  P  S  E  I  T  V  R  W  L  V
1441 AATGTGTCCCCTCTGAGATTACTGTACGGTGGTTAGT

H  D  E  A  Q  P  N  T  T  Y  N  T  V  V
     ACATGATGAAGCGCAGCCTAACACAACTTATAATACTGTGGTT
```

FIG 6E

```
     T  G  L  C  R  T  I  D  R  H  R  N  L  L
     ACAGGTCTCTGCCGACCATCGATCGCCATAGAAATCTCC

S  R  I  P  V  W  D  N  W  T  K  T
1561 TCAGCCGCATTCCAGTATGGACAATTGGACGAAAAC

K  Y  T  C  R  L  I  G  Y  P  F  D  E  D
     AAATATACGTGCAGACTCATAGGCTACCCCTTCGATGAAGAT

K  F  Q  D  S  E  Y  Y  D  A  T  P  S  A
     AAATTTCAAGATTCGGAATATTACGATGCAACTCCATCTG

R  G  T  P  M  V  I  T  V  T  A  V
1681 CAAGAGGAACACCCATGGTTATTACGGTTACGGCAGT

L  G  L  A  V  I  L  G  M  G  I  I  M  T
     TTTGGGATTGGCTGTAATTTTAGGGATGGGATAATCATGACT

A  L  C  L  Y  N  S  T  R  K  N  I  R  L
     GCCCTATGTTTATACAACTCCACACGAAAAAATATTCGAT
     *

1801 TATAATCTCATTGTTATGTAGTTGTGATTTATTAAAC
     ATATTTTTATAACTCTAGTATTCTCCGAGTACTTATATATT
```

FIG 6F

TATTGTCAGACACAATAAATGCAATAGTGGAGAAACGTGAGG

1921 GGAGTCTGTAAACAGAATACGTAATCATCTATTG

AATAAAAGATTGTGGTATAAATGAAGATAGCCGCAAGTCATTC

CAAGCTCTCCATTCTATTTAAACAATGTACAGTTTAAAGT

FIG 7A

```
  1 GAATTCTTGTAAAATATCATTAATTCCGCTACCAACGGGTTCCTTTTTTCACATAGCTG
    F  E  Q  L  I  D  N  I  G  S  G  V  P  E  K  K  E  C  L  Q

61 CTGCTCCGTAGTTATCTTTTTTGCTGGAACCATTCCCCAGGAAGTACGGGTCATTCTC
    Q  E  T  T  I  K  K  A  P  V  M  E  G  P  F  Y  P  D  N  E

121 AGAAATGGTCCTAGCGGATCTCTTCCGAGGGTTATTCTCCGAGTATTCGCTATCCCGTTT
    S  I  T  R  A  S  R  K  R  P  N  N  E  S  Y  E  S  D  R  K

181 ATTATTTTCTCAAGAGCCGAAATCAAGGCATCTAAGCGTGAAACAACAGTCTGCTCATG
    N  N  K  E  L  A  S  I  L  A  D  L  R  S  V  V  T  Q  E  H

241 TAATGATGGATACTGTATAGGATACGTTCCAGCCCCAGGAAACTGGCCGAAGTTCGAACT
    L  S  P  Y  Q  I  P  Y  T  G  A  G  P  F  Q  G  F  N  S  S

301 ATAATAATTTGGATGCACGGGGTAAGTAGATGCGGCTTTGATAAGGAATATATGGGAA
    Y  Y  N  P  H  V  P  Y  T  S  A  P  S  Q  Y  P  I  Y  P  F

361 ACGCCCGCAGAAATTTGGGTCTTCGTAAAGAGCCCGGTCTGTAAGTGTGGTTCATCCCCGG
    R  G  C  F  N  P  D  E  Y  L  A  P  R  Y  T  H  N  M  G  P
```

FIG 7B

```
421 ACCCATAAAAGATTCTAGGCGAGGGTGTCGTTCGAATCCACGCGGCCAAATATCACGTCC
     G  M  F  S  E  L  R  P  H  R  E  F  G  R  P  W  I  D  R  G

481 TGGTGAACATTCGTGAGTAGAGTCCCGCGACCTACGGGAAAACTCTCGTGATGGCGACAC
     P  S  C  E  H  T  S  D  R  S  R  R  S  F  E  R  S  P  S  V

541 GGGTCTCCGGTCGTTATCTCTGCGGGCTGATGCCGCAAGAGACTCGCATACTTCTCGAA
     P  R  R  D  N  D  R  R  A  S  A  A  L  L  S  A  Y  K  E  F

601 TGGGACATAGACCATATCTTCACGAGATGCGAACGGTGAAGCTCCGTTTTTGTTTGCAA
     P  V  Y  V  M  D  E  R  S  A  S  P  S  A  G  N  K  T  Q  L

661 GAACTGGCCGGAGCATGTCGCCGACTCCATGGCTGGAACGTGTGTTGCCCGACGGTTG
     F  Q  G  S  C  T  A  S  E  M  A  P  V  H  T  Q  G  S  P  Q

721 CTGACTCTCGCTTATATCGAAGCTTGGGCCGTTGCGTAGAAACTGAACGGTCTTTAAT
     Q  S  E  S  I  D  F  S  P  A  T  Q  T  S  V  S  R  D  K  I

781 AGCATTCTCAGGAGTCTCTTCGGAGTGTTCCTTAATCCCTATGGTTATTACCTCATTCGC
     A  N  E  P  T  E  E  S  H  E  K  I  G  I  T  I  V  E  N  A

841 TTGTAAATATTCGGGTTGTAAACAGCTGCGTCGCGTTTCAAACAGGTACC
     Q  L  Y  K  P  N  Y  V  A  A  M  E  R  R  T  K  L  C  T  G

901 CCTATCCATCAAAAACGCCCGTGAATAAATTCTTCATCAGGACTCGCGTAATTTCTGG
     R  D  M  L  F  A  G  H  I  F  K  K  M  L  V  R  T  I  E  P
```

FIG 7C

```
 961 TCGCGACAACTCTCTAGGACTTCTGCACATTTCTCACGTGTAGCTATTTCATACAGCTG
      R  S  L  E  R  P  V  E  A  C  K  E  R  T  A  I  E  Y  L  Q

1021 TTCTTTAATTGGTGCGCTCAAATCATCAAATGCTCCAATAGCTTCCGAAGCGGTGGCCCC
      E  K  I  P  A  S  L  D  D  F  A  G  I  A  E  S  A  T  A  G

1081 GTAAATTGCTACCGTGCCTTCACGTCTACCCAACTCACAGAGCCCACGTGTGCAAAAAA
      Y  I  A  V  T  G  E  R  R  G  L  E  C  L  A  V  H  A  F  F

1141 ATCTTTTCCGGGCACTTCGTTCTTTTCAAGCCGCCTTGAAGAGAGCGATAGAGAAGGTAG
      D  K  G  P  V  E  N  K  E  L  R  R  S  S  L  S  L  S  P  L

1201 AATGTTGCTGAGAAGATAGAGAAATTTCTCTGTCTCCGTCAAAACCATCCCCTCTTCGGC
      I  N  S  L  L  Y  L  F  K  E  T  E  T  L  V  M  G  E  E  A

1261 ATTCGCAAAAAGAGCATCATCTTGCACGTAGCTTAAAAAATAGGTGCAAGAGCAGTTGA
      N  A  F  L  A  D  D  Q  V  Y  S  L  F  I  P  A  L  A  T  S

1321 CACGACACCCAAACAAAACAGTCCTCTCGGCAGTCTAAGATCGTCAGCACTGTACCTAC
      V  V  G  L  C  F  L  G  R  P  L  D  L  I  T  L  V  T  G  V

1381 CACGCAGGATGACTCGTGGTCAATGTTTATCGGAATTGTTCCAGGCAAAACTGGTAAAGC
      V  C  S  S  E  H  D  T  N  I  P  I  T  G  P  L  V  P  L  A

1441 CGATTTGCTTTGCTCCGAGTAAGCTTCATATTCTCGCCCGGCACTTTCTTGTGGTCATA
      S  K  S  Q  E  R  T  L  E  Y  E  R  G  A  S  E  Q  H  D  Y
```

FIG 7D

```
1501 TACTACCAAATAGCCGGCAACGAAGATATATTTGATGTCGACGTTCTCCGACATAGCGAG
      V  V  L  Y  G  A  V   F  I  Y  K  I  D  V  N  E  S  M <<ORF1

1561 ACCGACTCGACCCCGCAAAGTATCAACACACTGACAAACAGACGGACTGATCAGAAAGAT

1621 ATAACCCTTTTATTGTCTAAACAGAGACGCGATCGCGAAAATACTAAGCATTATCCATAT

1681 GTCACGTGATGTGGCAAGCATCCAAGACACATAAAATAGATCAGGTCAGAATCAGACTCC
                                                      *  V  G

1741 ACGTTGAATGTCCTCAATATTCCTTTCAAATGCTTTTTTTGCATCAAATACCTCAAGTAA
      R  Q  I  D  E  I  N  R  E  F  A  K  K  A  D  F  V  E  L  L

1801 CCTGGACACTCCCTCTTCAACGTCACCTGTCAATGAATCGTGTACCGCCAAAACAGCAGC
      R  S  V  G  E  E  V  D  G  T  L  S  D  H  V  A  L  V  A  A

1861 TGCCCCGCTACCCACATGTGACGTTTTTCTGAGATCAAGCTCAATTAGATTACAGAGGGA
      A  G  S  G  V  H  S  T  K  R  L  D  L  E  I  L  N  C  L  S

1921 GGAATAGTACTCCCCCAACCGCTACCGCTGTCGGTATTCCTTTAACGCGCCCCGTTATGCA
      S  Y  Y  E  G  L  R  V  A  T  P  I  G  K  V  R  G  T  I  C

1981 GAGTGCAGCTAAACCAGGAAAGAAACCAGTAACTTCACATCTGTTGTCATATATCTATACAT
      L  A  L  G  P  F  F  G  T  V  E  C  R  N  D  Y  R  Y  M
```

FIG 7E

```
2041 AGGTACAACATATTTCTCGAATAAAAAGAACAAGTTGTTGTCGCGACTGGCCATATCTTG
      P  V  V  Y  K  E  F  L  F  F  L  N  N  D  R  S  A  M  D  Q

2101 TCCATTGTCATCAAATGTGCTTGCGGTGGCTCTTGAGGGTCTTGACCCAGGGGACGGGCCA
      G  N  D  F  T  S  A  T  A  Q  P  R  S  G  P  A  V  P  W

2161 TTTAGCTGCCTCCTGTTCCGATTGGGTTCCAAGTGGCAATTCAAAGAACGCAGATGGCTG
      K  A  A  E  Q  E  S  Q  T  G  L  P  L  E  F  F  A  S  P  Q

2221 AAATCGATTGAGATGTGTGCTCGTATAGACATTACTATTAAACATTAGCTTTTGCAAGAC
      F  R  N  L  H  T  S  T  Y  V  N  S  N  F  M  L  K  Q  L  V

2281 TAGGAGCAGAGATATCGAGTCTATAACCGTTCGCACAAGCGGATCATCTTCATGAAGAAT
      L  L  L  S  I  S  D  I  V  T  R  V  L  P  D  D  E  H  L  I

2341 TAACGGCGTTCGTCTCGAAGGGAAAAATGGAAGCAGAGTTTCTTTCGTTATATCTCGTACTGTGGT
      L  P  T  R  R  S  P  F  F  S  I  S  L  A  A  I  P  D  D  F

2401 ACGAACAAAATCTGGATCTATTGGAAGCAGAGTTTCTTTCGTTATATCTCGTACTGTGGT
      R  V  F  D  P  D  I  P  L  L  T  E  K  T  I  D  R  V  T  T

2461 GGAAAGGGTCCCAGTACGCTTTAGCAATTGATACACTATGTGAGGATCGAACACTCCATT
      S  L  T  G  T  R  K  L  L  Q  Y  V  I  H  P  D  F  V  G  N

2521 CGAATATTTCTGCCGTCAATTGGGAAAAAAGTTTACGGGAGTTTTGACCGGTCAAA
      S  Y  K  R  G  D  I  P  S  F  F  N  V  P  L  K  S  R  D  F
```

FIG 7F

```
2581 TGAAAATGTAACTGAGCCCCACTCGGCCCCGAATATCTTCCAGCATATAATTTAAATACGT
       S  F  T  V  S  G  W  E  A  R  I  D  E  L  M  Y  N  L  Y  T

2641 TGGAACATGTCTTAATGCATCTTCAAATATAGAAAACATCAAGACCATGTCTAATGTTGA
       P  V  H  R  L  A  D  E  F  I  S  V  D  L  G  H  R  I  N  S

2701 AGCAGATTGTCTAGACCGCGAGTAGTGCAGTAAGCATAAACAGTAGCCTCGAATCCGCT
       A  S  Q  R  S  Y  H  L  L  C  L  V  T  A  E  F  G  S

2761 ATATTGTCGAGTCCCAGCATAAATTTCCATCGCCAGTCGCAGCCTCGAATAGCCGTTT
       Y  Q  R  T  G  A  Y  I  E  M  A  S  R  L  A  R  I  A  T  K

2821 CATAAACCGCCCCGAGATGCGCGTGTCTCCCATTACATTCAAAACCCTAGCGATAGCTTT
       M  F  R  G  S  I  R  T  D  G  M  V  N  L  V  R  A  I  A  K

2881 ATTGTTATCTAGGAGCTGAGTCTGTAGCGCGGAACCAAGACCCGAATCCCAGCCGGCC
       N  D  L  L  Q  T  Q  L  A  R  F  W  S  G  F  G  L  R  G

2941 ATTGCCAGCAATAGCAAACGAAGTTGTCAGAAAATCTACTTGAAAATCTGTATTAAAGT
       N  G  A  I  A  F  S  T  T  L  F  D  V  Q  F  D  T  N  F  T

3001 TAATGGTTCTCCATTCTTAACTATCCAAATTACGTTCGCAGGGACATCCTTCGCCAGGCGC
       L  P  E  G  N  K  V  I  W  I  V  N  A  P  V  D  E  G  P  A

3061 ACGGATGTCTAGTGTTTTATAAGACCCAACAATGTCCTTCCTCCTGCACGGCCCGCTGGGC
       R  I  D  L  T  K  Y  S  G  V  I  D  K  E  Q  V  A  R  Q  A
```

FIG 7G

```
3121  TAAATCATCCAAGACATCAATTACAGTCTCTCTAGGGGATATTCAATAGTTTGCAATGCCGA
       L  D  D  L  V  D  I  V  T  E  L  P  Y  E  I  T  Q  L  A  S

3181  TGAGACATGTACGGGAACAGTAGCGCTCATATTTCCAGTTGCTCTAAAGCTGCCTTGGC
       S  V  H  V  P  V  T  A  S  M  N  E  L  Q  E  L  A  A  K  A

3241  AGCCCTGTTCCGCCTTTCCAGATCTTCAATCCTTGCACGATTGGTCATGATTTCTGCGTC
       A  R  N  R  R  E  L  D  E  I  R  A  R  N  T  M  I  E  A  D

3301  TATTAGAGTTCCTTCGAAAAGCTTAGATGCATATATTACTCGAGCCTTCCGCGCAGGAGAT
       I  L  T  G  E  F  L  K  S  A  Y  K  S  S  G  E  A  C  S  I

3361  AAAGTTTAAACGATCGGCTAAAACCATCAAGGTAGACGGCTTGTTGCTGTCCTTTGGTAA
       F  N  L  R  D  A  L  V  M  L  T  S  P  K  N  S  D  K  P  L

3421  ATTCATAGGTTCGAATCTCGGGTCGAAACATGGTTCGGACAAGTTTTTGGACTCCTCCGTA
       N  M  P  E  F  R  P  R  F  M <<ORF 2
                                    *  L  N  S  D  P  D  F  C  P  E  S  L  N  K  S  E  E  T  S

3481  GAAGTGGAATAGCTCGCGGGTTGGTTGCGGACTCTTTTCCCACGCCGACGAAAACAAT
       T  S  Y  S  A  P  K  T  A  S  E  K  G  V  R  S  S  F  L  A

3541  GCAGCTACGGTTTGTAAGGCTGAAGGGCGGGAGACGCTAGATCCGCATTCTTTGCACTT
       A  V  T  Q  L  A  S  P  A  P  S  A  L  D  A  N  K  A  S  E
```

FIG 7H

```
3601  TCTTGTTGATACTTACTGCGCGCATGCGACACGCGTGGCTCTTAATTTCGCGCAGAAAGTC
        Q  Q  Y  K  S  R  A  H  S  V  R  P  E  L  K  A  C  F  T  K

3661  TTTAAATACTGGCTTTCTGGTAGAGTGACAAAGAAAAGCTCAGACGATACATTTATA
        L  Y  Q  S  R  T  A  L  T  V  F  F  L  E  S  S  V  N  I  V

3721  ACCGTTTCCCCAACCGTTTTTACCGCCAAGATGTTCATCCCCCGTTGAGCAACAAATACC
        T  E  G  V  T  K  V  A  L  I  N  M  G  R  Q  A  V  F  V  L

3781  AGTAGAGAAAGAATCTTTACTTTCTCAGTGCCAGGAACAGCCAGATTCTCCAACAATCGT
        L  S  L  I  K  V  K  E  T  G  P  V  A  L  N  E  L  L  R  A

3841  GCAGAATCGCGAAGTTGGAGAGTGCCAGTATATCCTTGTCTTAATTTACTTTCAGTCATC
        S  D  R  L  Q  L  T  G  T  Y  G  Q  R  L  K  S  E  T  M  L

3901  AAAGATTTGGAAAAACGACACATGTTTTCAGTTCAATCACAATACATTTCATTTCATGTTGT
        S  K  S  F  R  C  T  K  L  E  I  V  I  C  K  M  E  H  Q  T

3961  GTCTCCAGCAAACAAATCAGCAATCAGGTTTCCGCAACCCTAGGTTCACTTCAAACATGACT
        E  L  L  C  I  C  D  P  K  R  L  G  L  N  V  E  F  M  V  V

4021  ACAATTTTGCCCCCGGCAGGTTTGCATTGGGGAATTATCGTATAGGCCAGCCTTCCGTCT
        I  K  G  G  A  P  K  C  Q  P  I  I  T  Y  A  L  R  G  D  G

4081  CCACCCCCTTCAAAGACTTCCTCCAGTGATCTGACGAGAGCTCGGTAAAAGCGATTATGG
        G  G  E  F  V  E  E  L  S  R  V  L  A  R  Y  F  R  N  H  C
```

FIG 71

```
                    ORF 4 >> M   A   V   A   G   A   V   K   T
4141 CAACGGATTCCGGCATTTAGTCTAGCCCGCAGAGATGGCCGTAGCTGGCGCCGTGAAAAC
          R   I   G   A   N   L   R   A   R   L   S   P   R   L   Q   R   R   S   F   K
       S   G   G   V   Q   F   C   S   E   F   E   N   D   D   S   D   F   R   R   V
4201 TTCCGGTGGTGTGCAGTTTTGCTCCGAGTTCGAGAACGATGACTCCGACTTTCGCCGCGT
          R   H   H   A   T   K   S   R   T   R   S   R   H   S   R   S   E   G   R   Q
       V   L   L   Y   V   D   G   P   F   G   V   G   K   T   V   T   A   K   T   L
4261 TGTACTTCTTTACGTCGACGGGCCATTCGGAGTCGGTAAAACAGTCACTGCAAAGACGTT
          V   E   K   R   R   R   A   M <<ORF 3
       M   Q   M   P   N   W   R   G   C   R   L   Y   L   A   E   P   M   Q   A   W
4321 GATGCAAATGCCAAATTGGAGAGGTTGCCGTCTATACTTAGCGGAACCTATGCAAGCATG
       R   Q   W   F   G   G   A   D   M   I   K   E   I   N   E   I   Q   T   L   K
4381 GCGCCAATGGTTTTGGCGGGAGCGGATATGATCAAAGAAATTAATGAAATACAAACCCTAAA
       A   S   G   K   L   E   C   R   E   A   S   P   V   A   V   A   E   V   Q   M
4441 GGCTTCCGGAAAACTTGAATGTCGGGAGGCGTCTCCGGTTGCCGTAGCGGAAGTTCAGAT
       T   I   A   A   P   L   R   I   M   N   H   V   I   Y   N   Y   L   G   S   E
4501 GACTATTGCTGCCCCACTAAGAATAATGAACCACGTCATTTATAATTATTGGGATCTGA
       R   C   Y   S   A   A   A   S   G   P   D   D   V   L   F   L   V   D   R   H
4561 ACGCTGCTACAGCGCTGCATCCGGACCAGATGATGTCTTATTCCTCGTAGATAGGCA
```

FIG 7J

```
           P   L   A   A   C   L   C   F   P   V   A   Q   Y   L   S   G   A   L   E   F
4621   CCCACTCGCGGGCATGTTTGTGTTCCCTGTTGCACAATATCTAAGCGGAGCGCTCGAATT

G   D   L   I   T   L   L   S   G   I   P   D   I   P   T   H   S   N   I   V
4681   TGGAGATTTAATAACTTTATTGTCAGGAATTCCTGACATTCCAACACACTCCAACATTGT

L   M   D   L   D   I   C   E   Q   A   R   R   I   Q   R   G   R   P   G
4741   TTTAATGGATTTGGATATTTGCGAACAGGCACGGCGTATAATACAAAGGGGCGCCCAGG

E   T   V   D   W   T   Y   L   C   A   L   R   N   S   Y   I   C   L   M   N
4801   GGAAACGGGTCGACTGGACGTATTTGTGTGCATTACGTAACTCGTACATCTGCCTCATGAA

T   T   T   Y   L   Q   R   T   S   Y   P   A   L   L   K   E   Q   E   A   L
4861   TACTACCACCTACCTCCAACGTACATCTTATCCAGCATTGTTGAAGGAGCAAGAAGCCTT

T   S   A   T   L   L   K   F   K   R   E   C   L   E   T   A   T   V   P   E
4921   AACAAGTGCCACGCTCTTAAAATTCAAGAGAGAGTGCTTAGAAACTGCTACTGTTCCAGA

I   N   P   S   I   D   Q   T   L   F   A   I   L   A   F   D   Q   Q   N   V
4981   AATCAATCCTTCAATGATCAGACCAGACGCTATTGCAATATATTAGCTTTTTGATCAGCAAAATGT

H   G   E   R   L   K   T   V   L   S   F   V   V   Q   K   L   A   T   V   L
5041   TCACGGGGAAAGATTAAAAACTGTACTTTCATTTGTGGTTCAAAAACTCGCGACGGTATT

K   N   L   C   I   F   Y   L   P   A   H   G   L   T   P   E   A   C   A   L
5101   GAAAAACTTGTGCATTTTTTACTTACCAGCACATGGCCTCACCCCGGAGGCATGTGCACT
```

FIG 7K

```
      K   C   L   E   F   A   E   T   A   S   S   L   T   T   K   R   A   A   I   A
5161 GAAATGTTTAGAGTTTGCCGAGAGCGGCAAGTTCTCTTACAACCAAACGAGCGGCGATCGC

S   L   I   D   A   V   E   R   Y   N   A   D   M   G   S   *
5221 GAGCTTAATTGACGCAGTAGAGCGCTACAATGCTGATATGGGTTCGTAATGTTCCGCTTC

M   S   F   T   H   F   L   A   L   Y   S   F   L
5281 CATAATCCTTCACAATAAGAGTATGTCCTTTACTCATTTCCTTGCTTTGTACTTCATTCTT

L   E   R   A   W   L   H   Q   Q   P   A   P   M   G   H   A   R   E   I   F
5341 ACTCGAGAGAGGCGTGGCTTCACCAGCAACCCGCCCGATGGGACACGCGAGAGAAATATT
```

Figure 9

Figure 10 ILTV Ribonucleotide reductase.

HVT HOMOLOGUES OF VZV62/ HSV-1 IE 175

```
  S   N   V   V   R   Y   M   C   G   N   T   V   L
TCGAATGTGGTGCGATACATGTGCGGGAACACGGTACTC

FIG 12

HVT HOMOLOGUE OF RIBONUCLEOTIDE REDUCTASE (LARGE SUBUNIT)

```
Q   V   T   E   V   S   E   G   F   A   P   L   F
CAAGTGACCGAGGTTAGCCGAAGGATTTGCCCCTTTGTTCA
         10            20           30          40

S   N   M   F   S   K   V   T   S   A   G   E   L   L
GTAACATGTTCAGCAAGGTGACAAGTGCCGGGGAACTGCT
         50            60           70          80

R   P   N   S   Q   L   M   R   E   L   R   Q   I
TAGACCCAACAGTCAATTAATGCGGGAGCTGAGACAAATA
         90           100          110         120

Y   P   D   N
TATCCCGATAAT
        130
```

FIG. 13A

MDV HOMOLOGUE OF RIBONUCLEOTIDE REDUCTASE ( LARGE SUB-UNIT )

```
         G   I   M   E   G   S   D   V   P   T   E   K   S
        GGGGATAATGGAAGGAAGTGATGTACCGACGGAAAAATCT
                 10        20        30        40

H   S   G   R   E   R   N   R   S   M   G   I   G
CATTCTGGCCGAGAACGTAACAGATCGATGGGCATCGGGCG
         50        60        70        80

V   Q   G   F   H   T   A   F   L   S   M   G   L   D
TGCAGGGCTTTCATACAGCTTTTCTATCTATGGGTCTTGA
         90       100       110       120

L   C   D   E   R   A   R   S   L   N   K   L   I
TTTATGCGATGAACGCGCTAGATCCCTCAACAAGCTAATT
        130       140       150       160

F   E   F   M   L   L   E   A   M   T   V   S   C
TTTGAATTCATGTTATTGGAGGCGATGACAGTTAGTTGCG
        170       180       190       200

E   F   C   E   R   G   L   P   P   F   A   D   F   S
AATTCTGCGAACGAGGCCTGCCCGTTTGCTGATTTCTC
        210       220       230       240
```

FIG 13B

```
N  S  Y  Y  A  R  G  R  L  H  F  D  G
TAACAGTTATTATGCACGAGGACGTCTGCATTTCGATGGG
        250       260       270       280

W  A  N  V  E  L  A  A  V  E  E  W  N
TGGGCTAATGTAGAATTGGCTGCAGTGGAAGAGTGGAATA
        290       300       310       320
```

FIG 14

MDV HOMOLOGUE OF RIBONUCLEOTIDE REDUCTASE ( SMALL SUB-UNIT )

```
    L   D   V   E   A   I   L   C   Y   V   R   Y   S
   TATTGGATGTTGAAGCAATATTATGTTACGTTACAG
            10          20          30          40

R   G   Q   T   E   R   I   D   M   P   P   I
   CCGCGGACAGACTACTGAAAGAATAGATATGCCACCTATT
            50          60          70          80

Y   N   E   P   K   P   T   A   D   F   P   H   A   L
   TACAACGAACCTAAACCTACAGCTGATTTTCCGCATGCAC
            90         100         110         120

T   A   S   N   N   T   N   F   F   E   R   R   N
   TGACAGCTTCAAATAATACCAACTTCTTTGAGAGAAAA
           130         140         150         160

T   A   Y   S   G   S   V   S   N   D   L   *
   TACTGCATACTCTGGAAGCGTGTCAAACGATCTTTAA
           170         180         190
```

FIG 15

HOMOLOGUE OF HSV-1 IE-175

```
  P   I   P   V   Y   V   E   E   M   K   D   Y   A
CCCATTCCCGTCTATGTAGAGGAAATGAAAGATTATGCCA
         10          20          30          40

K   Q   Y   D   A   L   V   N   S   L   F   H   K   S
AACAATACGACGCTCTCGTAAACTCTCTTTGTTTCACAAAAG
         50          60          70          80

M   K   V   N   P   L   N   W   M   H   H   G   K
CATGAAAGTAAATCCCTCTGAACTGGATGCACCACGGGAAG
         90         100         110         120

L   S   T   A   D   A   A   L   N   H   I   Y   V
CTGTCTACCGCCGATGCTGCCCTAAACCACATATATGTTC
        130         140         150         160

Q   K   F   Q   S   S   Y   D   S   P   G   A   A   V
AGAAATTCCAGAGTTCATACGATTCGCCCGGAGCGGCTGT
        170         180         190         200

T   G   T   V   N
AACTGGCACAGTTAACA
        210
```

FIG 16

MDV HOMOLOGUE OF HSV-1 IE-68

```
   S  D  Q  D  F  E  L  N  N  V  G  K  F
 CGTCCGATCAAGACTTTGAACTTAATAATGTGGCAAATT
        10        20        30        40

C  P  L  P  W  K  P  D  V  A  R  L  C
TTGTCCTCTACCATGGAAACCCGATGTCGCTCGGTTATGT
       50        60        70        80

A  D  T  N  K  L  F  R  C  F  I  R  C  R
GCGGATACAAACAAACTATTTCGATGTTTATTCGATGTC
       90       100       110       120

L  N  S  G  P  F  H  D  A  L  R  R  A
 GACTAAATAGCGGTCCGTTCCACGATGCTCTTCGGAGAGC
       130       140       150       160

L  F  D  I  H  M  I  G  R  M  G  Y  R  L  N
ACTATTCGATATTCATATGATTGGTCGAATGGATATCGACTAAA
      170       180       190       200

ID SEQUENCES

This is a continuation of copending application Ser. No. 07/669,391 filed on Apr. 29, 1991, now abandoned which is a 371 application of PCT/GB89/01075, filed Sep. 13, 1989.

The present invention relates to viral nucleotide sequences which may be manipulated to provide vaccines against disease.

BACKGROUND AND DESCRIPTION OF PRIOR ART

Herpesviruses are large double stranded DNA viruses consisting of an icosahedral capsid surrounded by an envelope. The group has been classified as alpha, beta and gammaherpesviruses on the basis of genome structure and biological properties [Roizman, B et al (1981) Inter-virology 16, 201–217]. Avian herpes viruses include Marek's Disease Virus (MDV) (a gammaherpesvirus) which causes a lymphomatous disease of considerable economic importance in chickens [reviewed in Payne, L. N. (ed) Marek's Disease (1985), Martinus Nijhoff Publishing, Boston] and Infectious Laryngotracheitis Virus (ILTV) (an alphaherpesvirus) which causes an acute upper respiratory tract infection in chickens resulting in mortality and loss of egg production.

A recent unexpected finding in our laboratory is that there is sufficient amino acid homology between MDV, ILTV and mammalian herpesviruses, particularly varicella zoster (VZV) and Herpes Simplex Virus (HSV) to allow identification of numerous conserved genes. These include the MDV and Herpesvirus of Turkeys (HVT) homologues of glycoproteins gB, gC and gH of HSV; the ILTV, MDV and HVT homologues of TK and ribonucleotide reductase genes and the ILTV homologue of gB and genes 34 and 35 of VZV [Buckmaster, A et al, (1988) J. gen. Virol, 69, 2033–2042.

Strains of MDV have been classified into three serotypes. Type 1 comprises pathogenic strains and their attenuated derivatives. Type 2 are a group of naturally-occurring non-pathogenic strains and type 3 is HVT. For more than a decade, vaccination with HVT has been remarkably effective in controlling Marek's disease. However, in recent years, new strains of MDV have been isolated which cause disease despite vaccination with HVT. Losses due to these 'very virulent' strains have occurred in parts of the U.S.A., Europe and the Middle East. Although the degree of protection can be improved by using a mixture of HVT, type 2 MDV and attenuated derivatives of very virulent strains for vaccination, the results have been erratic. These observations and the fact that there are MDV type-specific epitopes that are not shared by HVT or type 2 MDV have led us to the conclusion that improved vaccines might be constructed which are antigenically more related to MDV than existing vaccines. [Reviewed by Ross and Biggs in Goldman J. M. and Epstein M. A. (eds) Leukaemia and Lymphoma Research, Vaccine Intervention against Virus-Induced Tumour, p 13–31, Macmillan, 1986].

Infectious laryngotracheitis is also a worldwide problem. Sporadic outbreaks occur in which the severity of clinical symptoms varies considerably. Virus can persist in birds that have recovered and may be shed at intermittent intervals after recovery. An attenuated field strain is currently used as a vaccine. However, it has retained some degree of pathogenicity. Mortality due to the vaccine may reach 10% in young chicks.

A number of herpesvirus antigens have been shown to confer protective immunity when expressed in a recombinant vaccinia virus. These include the gB gene of HSV [Cantin E. M. et al (1987) Proc. Natl. Acad. Sci. U.S.A. 84, 5908–5912], gD of HSV [Paoletti, E. et al (1984) Proc. Natl. Acad. Sci. U.S.A. 81, 193–197] and gp50 of pseudorabies virus (PRV), a homologue of HSV gD [Marchioli, C. C. et al (1987) J. Virol. 61, 3977–3981]. Because of the absolute requirement of gB for virus penetration and infectivity and because it is conserved among herpes-viruses, gB and its homologues are important immunogens. Moreover, the presence of gB at the surface of infected cells has been shown to be an important target for humoral and cell-mediated immune responses [Blacklaws, B. A. et al J. gen. Virol. 68, 1103–1114 (1987); McLaughlin-Taylor, E. et al (1988) J. gen. Virol. 69, 1731–1734]. The recently described glycoprotein gH of HSV is also essential for infectivity and may also be an important immunogen [Desai, P. J. et al (1988) J. gen. Virol. 69, 1147–1156]. It has also been shown that gIII of pseudorabies virus (PRV), a homologue of gC, is a major target for neutralizing antibody and for cytotoxic T cells although it is a non-essential protein. Also of interest is the unexpected participation of immediate early proteins in T cell mediated cytotoxic reactions in cells infected with cytomegalovirus (CMV) [Kozinowski U. H. et al (1987) J. Virol. 61, 2054–2058]. Similar antigens could play an important role in the rejection of latently infected and transformed lymphocytes in Marek's disease since immediate early RNA transcripts have been detected in lymphoblastoid cell lines established from Marek's disease tumours.

Although many recombinant vaccines have been constructed using the poxvirus vaccinia as a vector, there are also reports of the use of herpesviruses as vectors for the expression of foreign genes. Thus hepatitis antigen has been expressed in HSV [Shih, M. F. et al (1984) Proc. Natl. Acad. Sci. U.S.A. 81, 5867–5870] and human tissue plasminogen activator has been expressed in PRV [Thomsen, D. R. et al (1987) Gene 57, 261–265. In both cases, foreign genes were inserted in cloned fragments of non-essential herpes genes which were then introduced into the virus vector by homologous recombination. The hepatitis virus gene was fused to a herpesvirus promoter and the recombinant DNA was inserted within the TK gene of HSV. Homologous recombination following co-transfection of the recombinant DNA and wild-type HSV DNA resulted in TK- virus clones that expressed the hepatitis antigen.

In the case of PRV, the gX gene mapping in $U_s$ was used as the site for insertion of the foreign gene. The strategy used involved insertion of the TK gene of HSV in the gX gene of a PRV mutant that had a defect in its TK gene resulting in a TK positive virus. The human tissue plasminogen activator gene was then inserted within a cloned fragement of HSV TK and the recombinant was introduced into the PRV mutant by homologous recombination. TK- virus was selected which expressed the human gene (Thomsen et al as above). Similarly, VZV has been used as a vector [Lowe et al (1987) Proc. Natl. Acad. Sci. U.S.A. 84, 3896–3900].

Several herpesvirus genes have also been shown to be associated with virulence and to be non-essential for growth in vitro. These include the TK genes of HSV [Jamieson, A. T. et al (1974) J. gen. Virol. 24, 465–480; Field, H. and Wildy, P., (1987) J. Hygiene (Cambridge) 81, 267–277] and of PRV. Indeed it has long been known that PRV is readily attenuated by deletion of TK activity [Tatarov, G. (1968) Zentralbl. Vet. Med 15B, 848–853]. Furthermore, attenuation of the Bartha strain of PRV has been attributed to a defect in gI, a non-essential structural glycoprotein mapping in $U_s$ [Mettenleiter, T. et al (1987) J. Virol. 61, 4030–4032].

Genes of HSV mapping in the internal repeat region (TRS) flanking the long unique sequence have also been associated with pathogenicity [Rosen, A. et al (1986) Virus Research 5, 157–175; Thompson, R. L. et al (1983) Virology 131, 180–192.] Several additional genes of HSV have been shown to be non-essential for growth in vitro although it is not known whether they are associated with virulence. These include UL24 (Sanders, P. G., (1982), J. gen. Virol. 63, 277–295, large subunit of ribonucleotide reductase (Goldstein D. J. and Weller, S. K. (1988) J. Virol. 62, 196–205), gC (Draper K. G. et al (1984) J. Virol. 51, 578–585), dUTPase (Fisher, F. B. & Preston, V. G. (1986) Virology 148, 190–197), and $U_L$ 55 and $U_L$ 56 (MacLean, A. R. & Brown, S. M. (1987) J. gen. Virol. 68, 1339–1350).

Moreover there is evidence that several genes of HSV mapping in $U_s$ are also non-essential for growth in vitro [Weber, P. C. et al (1987) Science 236, 576–579].

SUMMARY OF THE INVENTION

One aspect of the present invention provides a nucleotide sequence substantially free of the sequences which would adjoin it in the wild-type virus associated with the sequence, the sequence being selected from the group consisting of:

(a) the HVT homologue of the HSV gB gene,
(b) the HVT homologue of the HSV gC gene,
(c) the HVT homologue of the HSV gH gene,
(d) the TK gene of ILTV,
(e) the ILTV homologue of the HSV gB gene,
(f) ORF2 of ILTV,
(g) ORF3 of ILTV,
(h) the ribonucleotide reductase (large subunit) gene of ILTV,
(i) the ribonucleotide reductase (large subunit) gene of HVT,
(j) the ribonucleotide reductase (large subunit) gene of MDV,
(k) the ribonucleotide reductase (large subunit) gene of MDV,
(l) the HVT homologue of the immediate early gene IE-175 of HSV-I, and
(m) the HVT homologue of the immediate early gene IE-68 of HSV-I, and minor variations thereof.

Each of sequences (a) to (m) may be associated with further elements such as suitable stop and start signals and other 5' and 3' non-coding sequences, including promoters, enabling expression of the sequence. Such further elements may be those associated with the sequence in its naturally-occurring state or may be heterologous to that sequence.

In particular the promoter may be one associated with one of the sequences (l) and (m) above.

The term "minor variations thereof" is intended to include changes in the nucleotide sequence which do not affect its essential nature, for example minor substitutions of nucleotides for one another. In the case of sequences which are intended for insertion into a vector to encode an antigen, the "essential nature" of the sequence refers to the (glyco) protein encoded. Conservative changes in the nucleotide sequence which give rise to the same antigen will clearly be included, as will changes which cause conservative alterations in the amino acid sequence which do not affect adversely the antigenic nature of the antigen, in particular, antigenic portions of the antigen sequences may be used alone, for example the regions corresponding to nucleotides 273–320 or 867–926 of HVT gH and minor variations thereof. These sequences and the peptides encoded thereby form a further aspect of the invention. In the case of a sequence which is an insertion site, it is necessary only that the sequence should be non-essential for the infectivity and replication of the virus and have sufficient homology with the defined sequence to enable recombination to occur. Thus an insertion of one nucleotide into the sequence could completely change the reading frame from then on in a downstream direction. In the case of an antigen-encoding sequence this would usually alter the amino acid sequence undesirably (depending on where the frameshift occurred), but in the case of an insertion site, the degree of homology would be almost the same, thereby allowing recombination to take place with almost the same ease.

Generally speaking, in an insertion site, if a nucleotide homology of at least 75% is present, the sequence is regarded as a "minor variation". Preferably, the sequence is at least 80, 85, 90, 95 or 99% homologous.

It will be appreciated that such degrees of homology relate to substantially the entire portion of each sequence (a) to (m) defined above. Shorter sequences may be used as probes in the identification or isolation of such longer sequences, but in this case the degree of homology will in general need to be greater in order to ensure accurate hybridisation.

Thus, a further aspect of the invention provides sub-sequences of at least 13 nucleotides having at least 90% (preferably 95%, 99% or 100%) homology with at least one portion of any of the said sequences (a) to (m) above.

In the above list, sequences (a) to (c), (e), (f), (l) and (m) are useful for expressing viral antigens. Sequences (b), (d) and (g) to (k) and, in addition, the TK region of MDV are useful as non-essential sites suitable for insertion of antigen-expressing genes. Thus, sequence (b) is useful for both functions.

The sequences may readily be isolated from naturally-occurring ILTV, HVT and MDV viruses, using the sequence information given herein and standard techniques, for example involving the preparation of oligonucleotide probles and use thereof to hybridise to the naturally-occurring DNA.

Antigenic ILTV and HVT sequences, i.e. sequences (a) to (c), (e), (f), (l) and (m) above, may be expressed in any suitable host and, in particular, in HVT or MDV. Suitable non-essential sites for insertion of one ILTV sequence include the MDV homologue of the HSV gC gene, the HVT homologue of the HSV gC gene, the TK gene of HVT or MDV, the ribonucleotide reductase (large subunit) gene of HVT or MDV and the ribonucleotide reductase (small subunit) gene of MDV.

A second aspect of the invention provides insertional or deletional mutants of MDV, HVT and ILTV as follows:

(i) for HVT, a mutation in the region homologous to the HSV gC gene or in the ribonucleotide reductase gene or the TK gene,
(ii) for MDV, a mutation in the region homologous to the HSV gC gene or in the ribonucleotide reductase (small subunit) gene or in the ribonucleotide reductase (large subunit) gene,
(iii) for ILTV, a mutation in the TK gene, ORF3 or the ribonucleotide reductase (large subunit) gene.

Each mutation may be in the coding or non-coding sequences of the regions identified.

Such mutant forms of HVT, MDV and ILTV may be used as, or created in the course of preparing, viral vectors for heterologous antigen-encoding sequences, or indeed as vectors for any other sequence which one wishes to express in a fowl in which the vector will replicate. Such sequences include, but are not limited to, (a) to (c), (e), (f), (l) and (m).

By "heterologous", we mean that the antigen-expressing sequence has not previously been found in the same place in relation to the remainder of the viral genome. For example, an antigen-expressing gene might be isolated from a virulent strain of ILTV and inserted into the TK region of a less virulent strain of ILTV; this insertion would be regarded as "heterologous" if it did not result in a naturally-occurring virus.

The heterologous sequence may alternatively be one coding for an antigen associated with any one of the following diseases: avian encephalomyelitis (epidemic tremor), avian influenza (fowl plague), avian leukosis, avian paramyxoviruses other than Newcastle disease (PMV2 to PMV7), avian reovirus diseases (enteric disease, tenosynovitis), chicken anaemia (caused by chicken anaemia agent), coccidiosis, egg drop syndrome (EDS76), fowl pox, infectious bronchitis, infectious bursal disease (Gumboro), inclusion body hepatitis (adenovirus), lymphoproliferative disease of turkeys, Newcastle disease, reticuloendotheliosis in chickens, reticuloendotheliosis in turkeys, rotavirus enteritis, turkey haemorrhagic enteritis and turkey rhinotracheitis. The sequence may alternatively encode paramyosin (a muscle protein common to all invertebrate parasites) or an antigenic part thereof, somatostatin or a growth-promoting part thereof or an immune regulator.

The vectors in accordance with the invention may provide multivalent vaccine protection. For example, a vaccine comprising ILTV carrying an MDV antigen coding sequence would be expected to protect against ILT and Marek's Disease.

Furthermore, the mutant ILTV viruses themselves are potentially useful in vaccines as attenuated viruses, without necessarily having a heterologous sequence inserted.

A convenient process for preparing the deletional or insertional mutants of the second aspect of the invention comprises simply introducing into a suitable cell, for example by co-transfection, a deletional or insertional mutant version of the appropriate region (for example, the TK region) and either whole viral DNA or a whole virus (for example the wild-type virus). The naked DNA of such viruses has been found to be infectious, provided that it has not been sheared. A calcium phosphate precipitate of the DNA is generally advantageous. Suitable cells include chicken embryo fibroblasts, chicken kidney cells and duck embryo fibroblasts, all preferably grown in sub-confluent monolayers in Petri dishes.

The transfected DNA and the whole viral DNA will then recombine with one another in the infected cells by homologous recombination and the desired recombinants can be screened for, for example by the detection of hybridisation to suitable probes or by an immunoassay using suitable antibodies to the gene product of the region in question.

For homologous recombination to take place, the viral DNA must replicate. At present, no cell-free replication system for MDV, HVT or ILTV is known. However, if such a system becomes available, then the process of the invention could be operated therein. The environment in which the replication and recombination occur is not critical.

The ILTV and HVT regions which were identified above as being responsible for encoding immunologically useful viral antigens can be inserted into suitable vectors, for example into HVT or into other vectors such as fowlpoxvirus, bacteria or fungi. In the case of viral vectors, especially herpesvirus vectors and poxvirus vectors, such insertion can be achieved by recombination betwen the antigen-encoding sequence, flanked by suitable non-essential sequences, and the vector's genome in a suitable host cell as described above. A promoter which is endogenous to the host will usually be used to control expression of the heterologous (viral antigen-encoding) sequence. In the case of bacteria and fungi, the antigen-encoding sequence may be inserted using known or yet-to-be-discovered techniques of DNA manipulation. A non-pathogenic strain of Salmonella may be used as such a host. The heterologous sequence may be inserted into the host's genome or be carried on an independently-replicating plasmid.

The flanking sequences which are used may comprise all, virtually all or less of the region into which the heterologous sequence is to be inserted. If all the region is employed, then the sequence of that region will clearly still be present in the resulting virus, but the function of that region will have been deleted. If less than the whole region is used as flanking sequences, then the result will be a structural as well as functional deletion. Either approach may be used.

Thus, the construction of deletional or insertional mutants of ILTV can yield improved vaccines. Alternatively, the expression of ILTV glycoproteins or other ILTV proteins engineered into HVT, fowl pox or other vectors can constitute effective vaccines.

To prepare a vaccine in which HVT, MDV or ILTV is the virus or vector, the virus is grown in suitable cells such as chick embryo fibroblasts in a standard culture medium which as 199 medium (Wellcome or Flow Laboratories) for 3 to 4 days at about 37° C. The cells are harvested by scraping from the surface of the culture or by trypsinisation and suspended in medium containing 1 mM EDTA or 10% dimethyl sulphoxide and in either case 4% calf serum before storage in liquid nitrogen in sealed ampoules.

For vaccination, typically, day-old chicks are injected intramuscularly with about 1,000 plaque-forming units. Immunity follows within a few days.

It should be noted that MDV and HVT are cell-associated viruses and are infectious only when present in cells. Thus, a vaccine based on such viruses will always include suitable infected cells.

The vaccines of the invention may be used to protect any fowl susceptible to ILTV or HTV, including commercially-reared poultry such as chickens, turkeys, ducks and quail.

Preferred aspects of the invention will now be described by way of example and with reference to the accompanying drawings, in which:

BRIEF DESCRIPTIONS OF THE DRAWINGS

FIG. 2 (parts A–R) shows the nucleotide sequence of the gB gene of the RB1B strain of MDV, with the numbering referring to the MDV nucleotides. the sequence of part of the HVT gB gene shown under the line. homologies indicated by vertical bars, and amino acid differences between MDV gB and HVT gB shown above the line:

FIG. 4 (Parts A–H) shows the nucleotide sequence of most of the HVT gH gene, with the corresponding amino acid sequence shown above the line;

FIG. 5 (Parts A–J) shows the nucleotide sequence of the HVT TK gene, with the numbering referring to the HVT nucleotides, the sequence of part of the MDV TK gene shown under the line, homologies indicated by vertical bars and amino acid differences between MDV TK and HVT TK shown above the line;

FIG. 6 (Parts A–F) shows the nucleotide sequence of the gC gene of the RBIB strain of MDV, with corresponding amino acids shown above the line;

Figure 8:
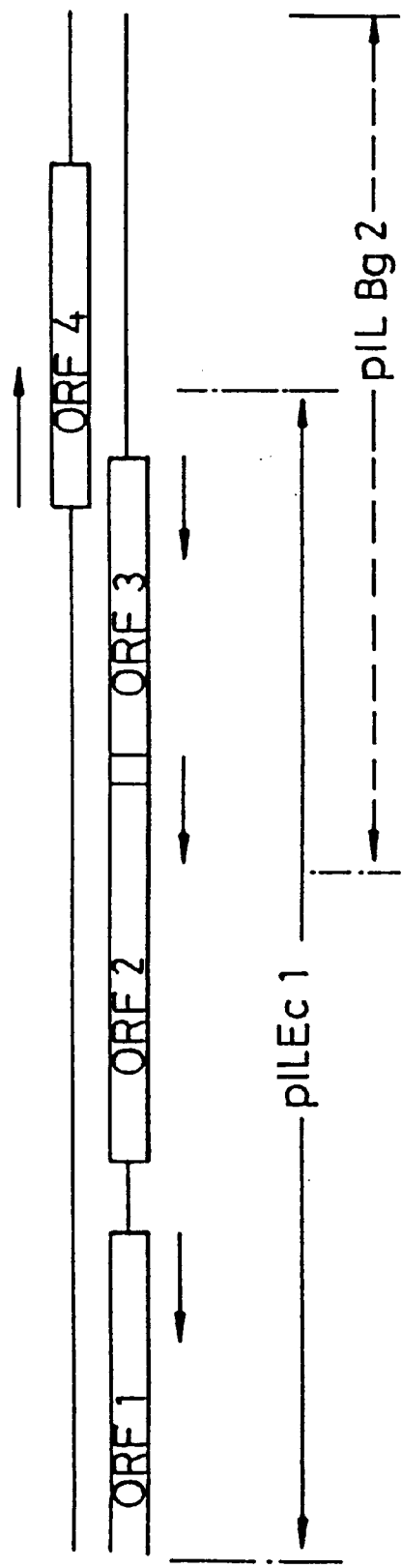
Figure 17:
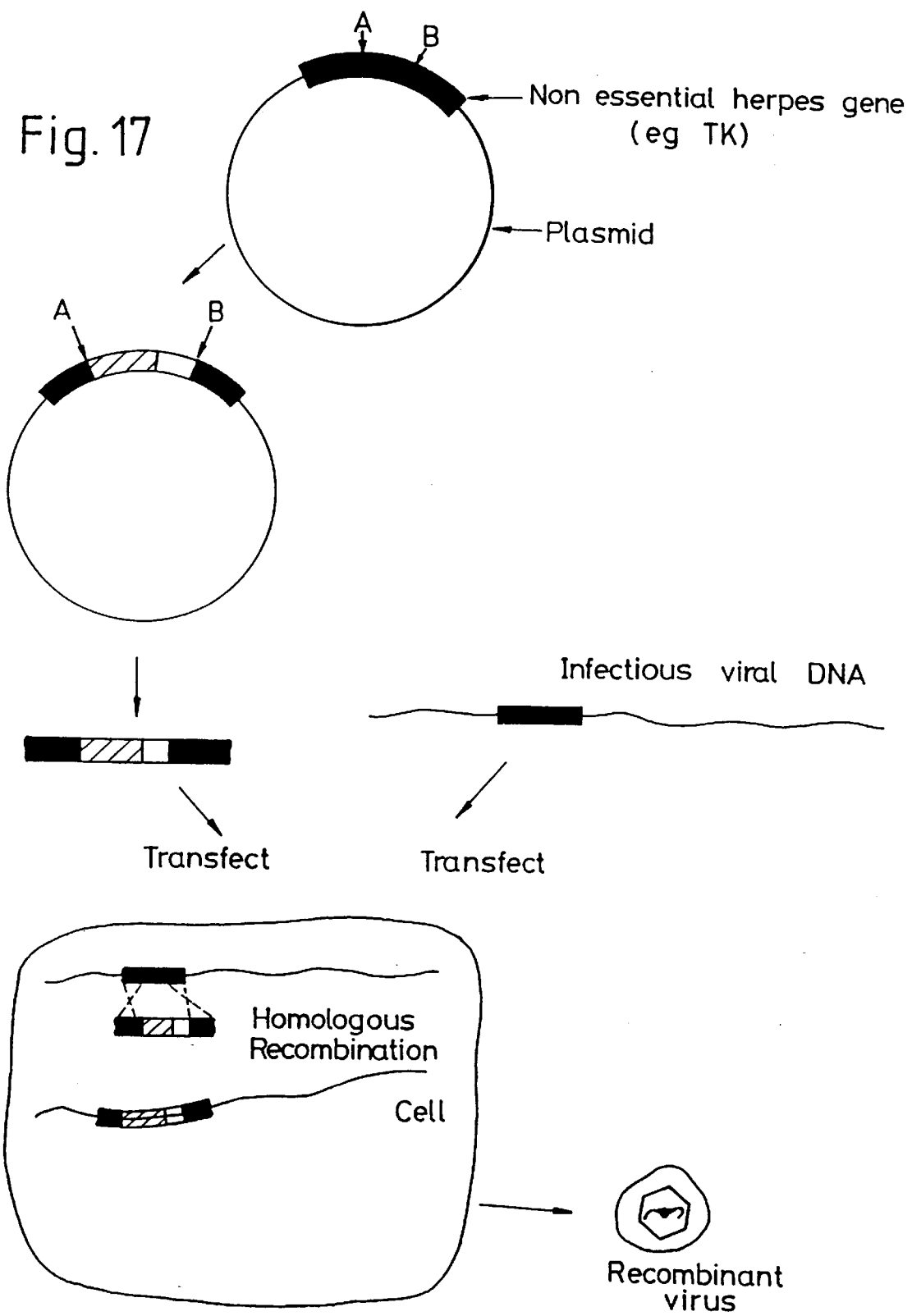
Figure 18:
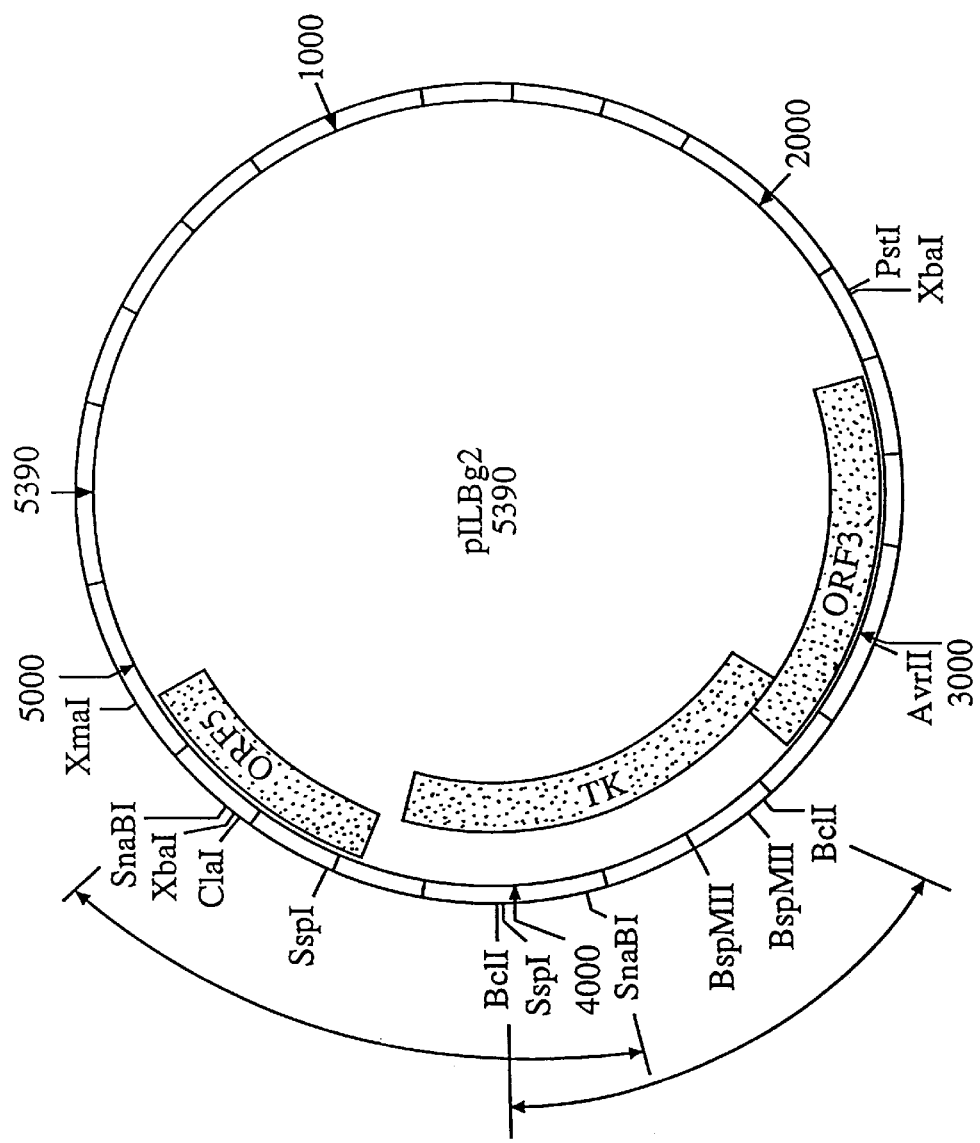

FIG. 7 (Parts A–K) shows the nucleotide and predicted amino acid sequence of a 5400 base pair region of the ILTV genome containing the TK gene cluster. Amino acid sequences predicted for the products of the major open reading frames (ORFs) are indicated in the single letter code below the sequence for the strand and above the sequence for the complementary strand. The locations of potential 'TATA' boxes are underlined. ORF 4 is the ILT TK gene sequence;

FIG. 8 is a representation of the gene organisation in the TK-containing part of the ILTV genome. Overlapping pUC 13 plasmid clones containing the EcoR1 (pILEc1) and BgIII (pILBg2) generated fragments of ILTV DNA are indicated. Open reading frames (ORFs) are depicted as open boxes with the direction of transcription indicated by the arrow;

Figure 9:
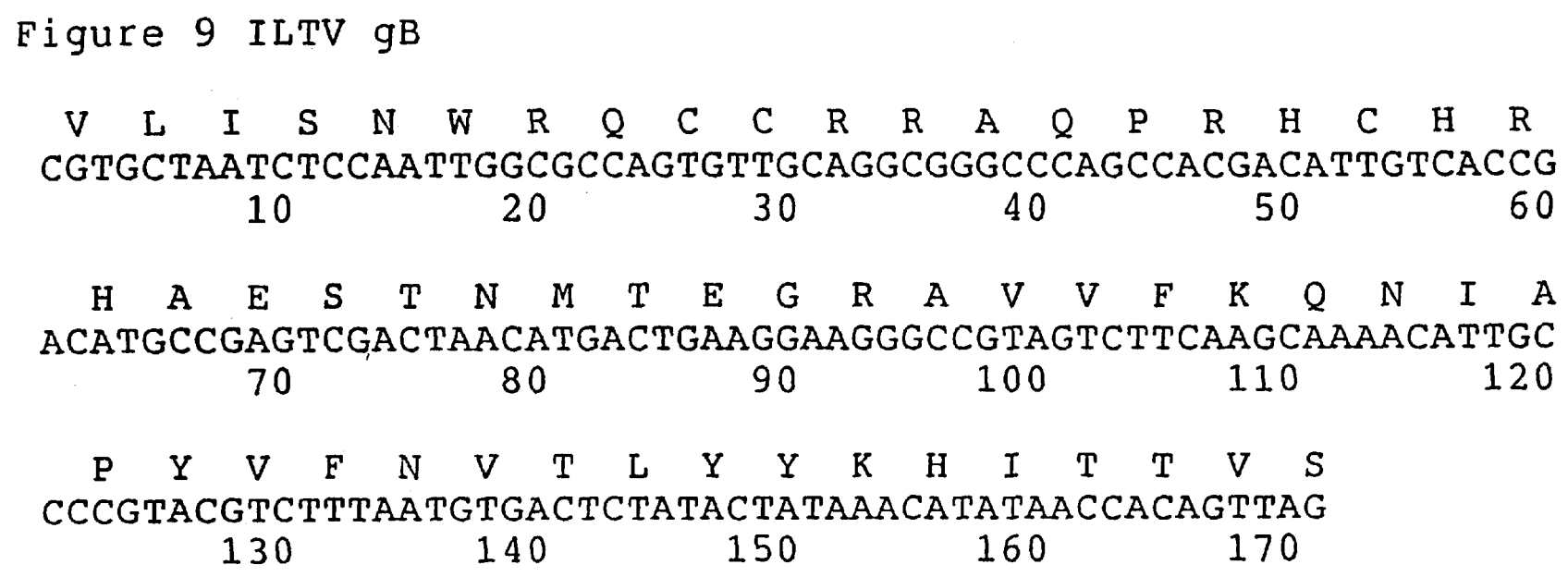

FIG. 9 shows part of the nucleotide sequence of the ILTV gB gene;

Figure 10:
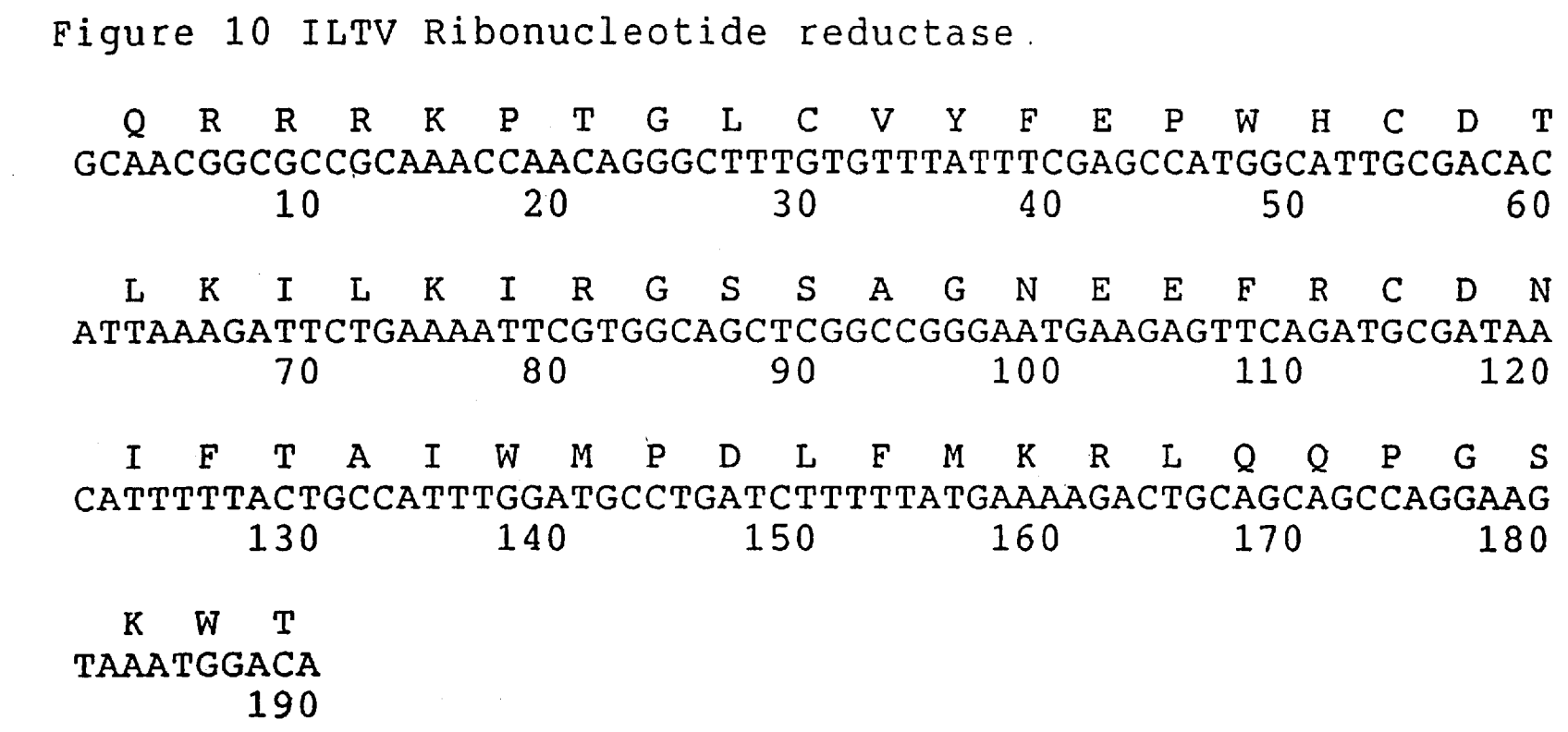

FIG. 10 shows part of the nucleotide sequence of the ILTV ribonucleotide reductase (large subunit);

FIG. 11 shows tart of the nucleotide sequence of the HVT homologue of the VZV62/HSV-1 IE 175 gene:

FIG. 12 shows part of the nucleotide sequence of the HVT ribonucleotide reductase (large subunit) gene;

FIG. 13 (Parts A–B) shows part of the nucleotide sequence of the MDV ribonucleotide reductase (large subunit) gene;

FIG. 14 shows part of the nucleotide sequence of MDV homologue of ribonucleotide reductase (small subunit) gene;

FIG. 15 shows part of the nucleotide sequence of the MDV homologue of the HSV1 IE-175 gene;

FIG. 16 shows part of the MDV homologue of the HSV-1 IE-68 gene:

FIG. 17 is a schematic representation of homologous recombination at a non-essential region of a viral genome and a homologous region of DNA cloned within a plasmid vector; and FIG. 18 is a map of plasmid pILBg2, showing restriction sites and the locations of the TK gene and ORFs :3 and 5.

EXAMPLES

General Approaches

Selected short sequences of the avian herpesviruses cloned in the bacteriophage vector M13 were used as probes to identify longer fragments that might contain the entire genes of interest. This was achieved by Southern blot hybridization of restriction fragments. Full details are given below.

Virus Strains.

The 'highly oncogenic' strain RB1B of MDV [Schat, K. A. et al (1982) Avian Pathol. 11, 593–605] was obtained from Professor B. Calnek, Cornell University, Ithaca, U.S.A. The virus received has been plaque purified in chicken kidney vells in tissue culture. It was passaged twice in SPF RIR chickens and 4 times in chick embryo fibroblasts (CEF). Its 'highly oncogenic' nature was demonstrated by a high incidence of gross tumours when inoculated in genetically resistant N-line chickens.

The FC126 strain of HVT [Witter, R. L. et al (1970) Am. J. Vet. Res. 31, 525—538], obtained from the Wellcome Research Laboratories, Beckenham, Ky., had been passaged 14 times in CEF. It was subsequently grown in duck embryo fibroblasts (DEF) and CEF in our laboratory. It was then plaque-purified and grown further in CEF. Viral DNA used for cloning in the present work was extracted from virus that had been passed 29 times since the original isolation.

The Thorne strain of ILTV was passaged twice in eggs, once in chicken kidney cells (CKC) and plaque-purified three times in CKC.

Tissue culture.

CEF were grown in roller bottles in 199 medium (Wellcome), supplemented with penicillin, streptomycin, Fungizone (Regd. T. M.) and calf serum as described previously [Ross, L. J. N. et al (1975) J. gen. Virol. 28, 37–47].

CKC were grown in 10 cm Petri dishes [Churchill, A. E. and Biggs P. M., (1967) Nature, 215, 528–530].

Isolation of MDV DNA.

Cell associated RB1B was inoculated onto confluent monolayers of CEF in roller bottles at a multiplicity of infection of approximately 0.001 plaque-forming units (pfu) per cell, and the cultures were incubated at 37° C. After 3 days, the medium was discarded and replaced with fresh 199 medium containing 2% calf serum. Cells were harvested for virus purification after 2 to 3 days when cytopathic effect was extensive. Virus was obtained by rate zonal centrifugation of the cytoplasmic fraction of infected cells [Lee, Y. S. et al (1980) J. gen. Virol. 51, 245–253]. Viral DNA was extracted by treating purified virus with sarcosyl, proteinase K and Tris buffer pH 9 overnight at 37° C. and purified by rate zonal centrifugation in glycerol gradients as described previously (Lee et al, 1980). High molecular weight viral DNA was precipitated with ethanol and resuspended in 10 mM Tris pH 7.5 im 1 mM EDTA (TE).

Isolation of ILTV DNA.

(a) Infected CKC were harvested 2–3 days after inoculation, washed in PBS, and resuspended in ice-cold TE by vortexing. Cells were lysed by addition of the non-ionic detergent NP40 (final 1%) vortexing and incubation on ice for 15 min. After treatment with RNAse, the preparation was centrifuged at 2000 rpm for 5 min in a bench top centrifuge (Centaur). The supernatant was collected and incubated at 37° C. for 30 min in the presence of SDS (final 1%) and proteinase K (final 0.5 mg/ml). The mixture was extracted twice with phenol-chloroform and once with chloroform and the DNA was then precipitated with ethanol and ¹/₁₀ vol of 3M sodium acetate.

(b) Viral DNA was also isolated from the media of virally infected cells in the following way. The media of infected cells were harvested at 2–3 days post infection and centrifuged at 3000 for 5 mins at 4° C. rpm in a bench centrifuge. The supernatant was collected and centrifuged at 19K rpm in an ultracentrifuge (Sorvall) for 1 hr at 4° C. The viral pellet was resuspended in TE, digested with RNAse A, then disrupted with SDS and proteinase K as described above. Finally, DNA was extracted from the disrupted virus as described above.

Cloning of MDV DNA.

One fg of MDV DNA was cut with the restriction enzyme BamH1 and ligated to BamH1-cut, dephosphorylated pUC13 DNA (Pharmacia). Competent *E.coli* strain TG1 cells were transformed according to standard procedures [Hanahan, D. (1983) J. Mol. Biol. 166, 557–580] and were grown in the presence of ampicillin and X-gal. White colonies were picked and tested for the presence or MDV inserts by hybridization to nick-translated MDV DNA [Grunstein M. and Hogness, D. S. (1975) Proc. Natl. Acad. Sci. U.S.A. 72, 3961]. Positive colonies were cultured in small volume and plasmid DNA isolated by the procedure of Holmes, D. S. and Quigley, M. [(1981) Anal. Biochem. 114, 193–297]. The size of the inserts was determined by electrophoresis of BamH1 digests of the recombinant DNA in agarose gels. Plasmids containing MDV inserts ranging from less than 1 to 18 Kbp were obtained.

Cloning of ILTV DNA.

EcoR1 and BglII libraries of ILTV DNA were obtained by cloning digests of viral DNA in pUC13 as described above.

Random sequencing of viral DNA.

Sonicated fragments of viral DNA were cloned into SmaI-cut, dephosphorylated M13.mp10 (Amersham International PLC) and plaques containing MDV inserts were identified by hybridization to MDV DNA. The sequence was determined by the dideoxy method [Sanger, F. et al (1977) Proc. Natl. Acad. Sci. U.S.A. 74, 5463–5467] using $^{35}$S dATP).

The same procedure was used to sequence cloned fragments of MDV, HVT and ILTV DNA except that plaques were identified by hybridization to labelled insert so as to avoid colonies containing pUC13 fragments.

Example 1 gB gene of MDV

Figure 1:
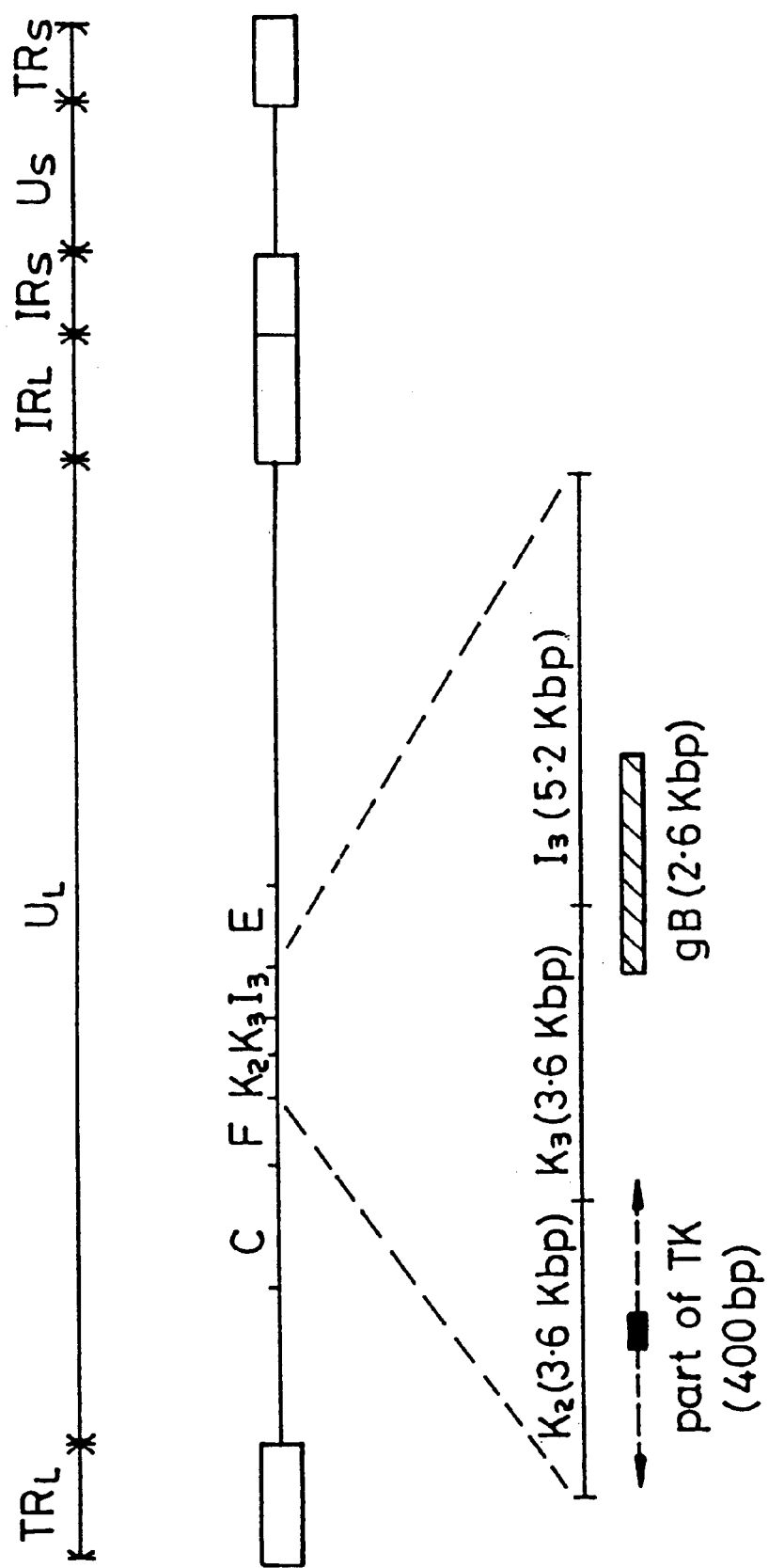
FIG. 1 is a map of the MDV genome showing in part the BamH1 site distribution and the location of the gB and TK genes.
Figure 3:
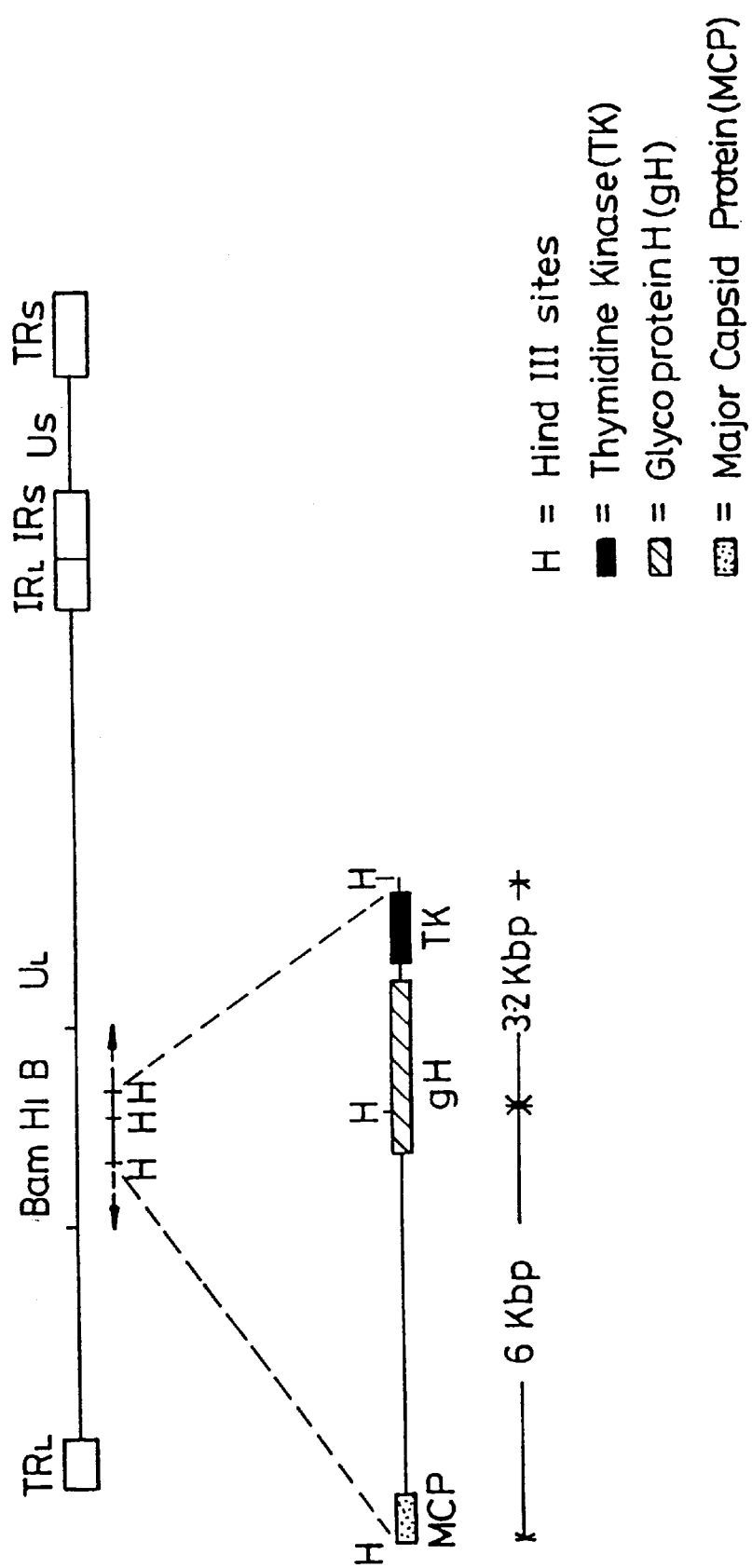
FIG. 3 is a map of the HVT genome showing the positions of the gH (hatched), TK (solid black) and major capsid protein (MCP, dotted) genes, with HindIII sites shown as "H"

An M13 clone of HVT homologous to the gB gene of VZV and HSV hybridized to BamH1 fragment I3 of MDV (see FIG. 1). Sequencing of this fragment obtained from a BamH1 library of the RB1B strain of MDV showed that two thirds of the gene, starting with the $NH_2$ terminus, was contained within I3. The remainder of the gene was identified in the adjacent restriction fragment K3. FIG. 1 shows the map position of the gene which is 2.6 Kbp long. Its mRNA has been estimated to be approximately 2.8 Kb. The translated protein is 865 amino acids long (FIG. 2). This includes approximately 20 amino acids which may be part of a signal sequence domain. The primary translated sequence of MDV gB has a few features in common with gB of other herpes viruses such as the alignment of cysteine residues and the presence of hydrophobic sequences which are presumably capable of spanning a lipid bilayer [Pellet, P. E. et al (1985), J. Virol. 53, 243–253]. However, MDV gB has only 48% amino acid similarity with gB of HSV and has many unique features such as the insertion of 23 amino acids (residues 1851–1920, FIG. 2) and the presence of extra sites with glycosylation potential. Comparison of the sequence of MDV gB with limited sequence data (702 bases) available for HVT gB (FIG. 2) has shown 76.9% nucleic acid similarity and 87.1% amino acid similarity between these two glycoproteins. Amino acid substitutions in HVT gB compared to MDV gB were particularly marked in a region (residues 1323–1433) equivalent to a domain of HSV gB associated with virus neutralization [Pellet P. E. et al (1985) as above]. Amino acid substitutions between MDV and HVT gB were also noted in other regions of unknown function.

Example 2 gH gene of HVT and gH gene of MDV

An M13 clone of HVT containing sequences homologous to HSV gH was isolated during our earlier work on gene identification and mapping (Buckmaster et al (1988) as above). This clone, when used as a probe, hybridized to a 6 Kbp HindIII fragment of HVT (FIG. 3). Sequencing revealed that this fragment contained approximately one quarter of the gH gene including the carboxy terminus. The adjacent HindIII fragment (3.2 Kbp) containing the remainder of the gH gene was identified by hybridization using a cloned HpaI fragment of HVT which overlapped the HindIII site. FIG. 4 shows the sequence of the coding region of the gH gene of HVT (2.3 Kbp) and flanking sequences. The % amino acid identity between the gH gene of HVT and its homologue in HSV1, VZV and EBV was only 20, 24 and 20 respectively (estimated from maximised amino acid overlaps of 630, 644 and 153 respectively).

Example 3

TK gene of HVT and TK gene of MDV

The whole coding region of the TK gene of HVT (1053 bp) was contained within the 3.2 Kbp HindIII fragment described above (FIG. 3). The sequence of the entire gene and flanking regions is shown in FIG. 5. Similarly the whole of the MDV TK gene is contained within the 3.6 Kbp BamH1 K2 fragment of MDV (FIG. 1). The sequence of MDV TK gene determined so far is shown in FIG. 5. Comparison of the MDV and HVT TK sequences indicates that the two genes have approximately 60% amino acid identity (estimated from 276 amino acid overlap). By contrast, the % amino acid identities between the TK gene of HVT and the TK genes of HSV 1, VZV and EBV are only 30, 27 and 24 respectively (estimated from amino acid overlaps of 320, 332 and 193 respectively). The predicted amino acid sequences of HVT and MDV TK show characteristic ATP and/or CTP binding site motifs described for a number of virus and eukaryotic proteins that are associated with phosphorylation (Gentry, G. A. (1985) Proc. Natl. Acad. Sci. U.S.A. 82, 6815–6819). These conserved sequences are examples of useful sites for insertion and expression of foreign genes and for producing TK- deletion mutants.

Example 4

A antigen gene of MDV (gP57–65) (gC homologue)

The A antigen gene is of interest in vaccine development both as an immunogen (it encodes a major glycopolypeptide product) and also because we have identified it as the homologue of HSV gC, a potential non-essential region. The A antigen gene was mapped within the BamH1 B fragment of MDV (Isfort et al 1987), and the nucleotide sequence determined for the GA strain of MDV (Coussens and Velicer, Abstract OP18.51, VII International Congress of Virology, Aug. 9–14, (1987) Edmonton, Canada; J. Virol. 62, 2373–2379). During the random sequencing studies described earlier (Buckmaster et al 1988), we identified an M13 clone (No. 130) which came from the A antigen gene. This clone was then used to identify a 2.3 Kbp EcoR1/PvuII fragment from the RB1B strain of MDV containing the A antigen. This fragment was cloned into a SmaI/EcoR1 cleaved pUC13 vector by standard protocols. One plasmid (pMB419) was sequenced by the M13 dideoxynucleotide method. The sequence of the MDV RB1B A antigen and the predicted amino acid sequence of the protein are presented in FIG. 6. The A antigen regions of MDV and HTV are non-essential genes and they can therefore be used as sites in MDV and HVT into which other genes can be inserted into the virus by homologous recombination. Several lines of evidence support this as outlined below.

1) During our study we isolated and sequenced another RB1B A antigen clone. This had one extra T residue in the string of T's 45 bases 3' to the A antigen ATG codon. This extra T would cause a frameshift which would make it impossible for the gene to encode functional A antigen. As it is probable that this gene was cloned from a replicating MDV, the results suggest that the A antigen is non-essential to the virus.

2) On conducting a similarity search it became clear that the MDV A antigen gene is the homologue of HSV gC and PRV gpIII glycoproteins. Both of these homologous genes are known to be non-essential [for the HSV homologue, see Rosenthal et al (1987) J. Virol. 61, 2438–2447].

3) Strains of MDV lacking A antigen as judged by agar gel diffusion tests [Churchill, A. E. et al (1969) J. gen. Virol. 4, 557–564] or producing low levels using the more sensitive 2D radio-immunoprecipitation (van Zaane, D. et al (1982) Virology 121, 133–146] have been reported.

Furthermore, in view of the fact that the A antigen is a major secreted glycoprotein, it may be a particularly suitable location for the presentation of foreign epitopes within the A antigen as soluble, secreted proteins. This may be achieved by cloning oligonucleotides encoding these epitopes in frame within the A antigen gene.

STRATEGIES FOR INTRODUCING GENES INTO HVT AND ILTV VECTORS

Two possibilities can be envisaged. 1) Insertion into non-essential genes of the vector. 2) Substitution of foreign gene for corresponding gene of the vector. This would be possible only in regions which already have substantial homology as may be the case between some genes of MDV and HVT.

Example 5

Insertion into non-essential genes of HVT, ILTV or MDV (a) Insertion at the TK locus of the vector.

1) HVT, ILTV or MDV may be used as vectors for insertion and expression of avian herpesvirus genes. In particular gB, gD, gH or gC of RB1B MDV may be inserted into ILTV. Also gB and BS-17 of ILTV may be inserted into HVT or MDV. One may use the promoter associated with the inserted gene or use heterologous promoters, including those of a different class of genes (for example the immediate early promoter to optimise expression of gB).

2) ILTV may be used as a general vector for the insertion and expression of genes unrelated to avian herpes viruses and likely to require manipulation of promoters for optimal expression.

The procedure to be used for gene insertion is substantially as described previously for the insertion of hepatitis antigen in HSV [Shih et al, 1984 as above].

MDV and HVT DNA obtained as described above is infectious provided that precautions are taken not to shear the DNA during extraction. Calcium phosphate precipitates of viral DNA prepared as described by Stow and Wilkie [(1976) J. gen. Virol. 33, 477] were added to sub-confluent monolayers of CEF. After absorption for 1 h at 37° C., culture medium was added and cultures were incubated for 1 or 2 days until confluent. Monolayers were then trypsinised, replated (1:1 or 1:2) in 199 medium (Wellcome) containing 2 to 4% calf serum and incubated at 37° C. until plaques developed, usually after 4 to 5 days. Approximately 200 plaques may be obtained per $\mu$g of HVT DNA and approximately 50 per $\mu$g of MDV DNA.

Restriction enzyme sites than could be used for the insertion of foreign antigens into the TK of HVT strain Fc-126 include: BanII, Bsp1286, DraIII, EcoRI, HincII, HpaI, NheI and NspbII.

Some of these enzymes also have sites in the plasmid vector into which the virus DNA fragments are cloned. Thus in order to linearize the clone DNA without also cutting within the vector, partial digests may be carried out.

None of the above enzymes should cause any disruption to flanking gene, HSV-1 homologues of which are known to play an important role in virus multiplication.

For homologous recombination and isolation of recombinant virus, genes of interest are inserted within non-essential genes such as TK or gC and co-transfected with wild-type viral DNA at molar ratios ranging from 10:1 to 2:1 as described above. Alternatively, intact wild-type virus may be used for co-infection.

Virus recombination may be detected by 'plaque lifts' which involve transfer of infected cells and released virus which have adhered to the agar overlay to nitrocellulose and hybridization of the denatured DNA released from the cells and virus to suitable probes as described by Villareal, L. et al (1977) Science 196, 183–185. Virus which hybridizes to the probe may be recovered from the monolayer.

A similar procedure may be used to isolate recombinant virus which expressed epitopes of interest. In this instance the nitrocellulose "plaque lifts" are treated with antibody and the presence of bound antibody revealed using a suitable detection system such as labelled protein A or phosphatase conjugated anti-globulin antibody.

The gene of interest with appropriate promoters is first inserted within the cloned TK gene (FIG. 7). The recombinant DNA is then co-transfected with infectious DNA of the vector in chick embryo fibroblasts or chicken kidney cells and TK- virus may be selected by growth in medium containing acyclovir [Ross, N. (1985) as above] or FMAU [Schat, K. A. et al (1984) Antiviral Research 4, 159–270]. Alternatively, or in addition, plaques are screened for the presence of the gene of interest using 'plaque lifts' on nitrocellulose and hybridization to any relevant labelled probe. Plaques are also screened for expression of the epitopes of interest using monoclonal antibodies or antipeptide antibodies.

The main advantage of this strategy is that the selection procedure increases the chances of obtaining virus recombinants containing the gene of interest. It also offers the opportunity of using different promoters for optimum expression. Thus the use of an immediate early promoter may allow expression in latently infected cells.

(b) Insertion at the gC locus of the vector.

Since the A antigen (HVT and MDV homologues of HSV gC) is not essential for virus growth in vivo and in vitro (see section on gC above) it is a potentially useful site for the insertion and expression of foreign genes. Moreover, since it is one of the most abundant antigens and is excreted, it may be particularly useful for enhancing the immunogenic properties of foreign proteins. The isolation of virus recombinants at this locus may be achieved by first inserting at least part of the gene of interest in frame within the gC gene and then co-transfecting with infectious viral DNA. Screening of virus plaques with sequence specific probes or with specific antibody allows the isolation of recombinants.

Example 6

Substitution of ILTV genes for their homologues in HVT

Substitution may be achieved by co-transfection of cloned ILTV sequences and infectious HVT DNA as described in Example 5. Substitution of genes derived from ILTV for their counterparts in HVT may be effected.

Recombinants expressing ILTV sequences and epitopes may be detected using ILTV-specific monoclonal antibodies or anti-peptide antibodies raised against unique ILTV sequences as described above.

The advantage of this procedure is that it is relatively simple and does not require manipulation of promoters. However, it may be limited to genes which share substantial homology.

Example 7

Strategies for obtaining TK- mutants of ILTV

Deletion mutants.

Deletions may be introduced within any suitable part of the gene, for example the domains of the gene that are required for its function as a phosphorylating enzyme such as ATP and CTP binding sites. This may be achieved by restriction enzyme digestion, for example with SnaB1 or BclI, and religation of appropriate fragments followed by co-transfection with infectious viral DNA or transfection into virally-infected cells. Reference may be made to FIGS. 7 and 8, and to the map of plasmid pILBg2 (FIG. 18), in choosing restriction enzymes and so on. TK- virus may be selected in the presence of acyclovir [Ross, N. (1985) as above] or FMAU [Schat, K. A. et al (1984) as above]. Plaque-purified clones may then be tested for the absence of the deleted portion of the TK gene by hybridization.

The deletion mutants of ILTV may be used themselves as attenuated viruses for vaccine preparation, or may have sequences for heterologous antigens inserted.

Insertional mutants.

A functional γ-galactosidase gene under the control of a herpesvirus promoter or any other suitable sequence or a single base is first introduced in a domain of the TK gene which is essential for TK activity. The recombinant DNA is then co-transfected with infectious viral DNA or transfected into virally-infected cells to allow homologous recombination to occur. Selection in the presence of acylovir or FMAU will yield TK- insertional mutants. If a β-galactosidase gene is introduced, mutants can be detected by the production of blue plaques in the presence of X-gal.

The TK gene and surrounding sequences may be sub-cloned into another suitable vector if necessary.

Example 8

Insertion of MDV RB1B gB gene into HVT (Not within the scope of the invention, but illustrates an analogous technique).

The HVT TK gene is cloned in the plasmid vector pUC13 to generate a plasmid, which may be termed pTK1B. This plasmid is linearised with, for example, the restriction endonuclease Rsr II which cleaves the plasmid only within the TK gene (nucleotide position 197 in FIG. 5, enzyme recognition sequence CGGACCG). The "sticky" ends thus generated are end repaired by standard techniques (see "Molecular Cloning: a Laboratory Manual", ed. Maniatis T., Fritsch E. F., and Sambrook J. Cold Spring Harbor Laboratory 1982).

The RB1B gB was originally cloned on two plasmids which were termed RB1B-BamH1-$I_3$ and RB1B-BamH1-$K_3$. (Note $I_3$ had lost one BamH1 site during cloning.) To generate a complete gB copy on one plasmid, both plasmids were cleaved with BamH1 and the fragments ligated. However, the complete gB gene was later obtained independently on an EcoRI/SalI fragment. Ross et al. J. gen. Virol (1989) 70, 1789–1804 provides further information regarding the manipulation of viral genes. Recombinants containing the desired configuration can be identified by restriction enzyme analysis of plasmid DNA's.

The recombinant plasmid is then cleaved with EcoR1, the ends are repaired and the plasmid is cloned into PTK1B prepared as above. The recombinant plasmid is then introduced into cells containing HVT virus (viral DNA) and homologous recombination will introduce the gB gene into the TK gene. HVT viral recombinants can be selected with acyclovir or FMAU or alternatively detected with labelled gB probes.

Example 9

RB1B gC (A antigen) gene into HVT

Blunt ended PTK1B is prepared as in Example 8. The RB1B gC is cleaved from the plasmid pMB419 (Example 4) with the restriction endonucleases EcoR1 and HindIII (site within the pUC13 polylinker). The sticky ends generated are again end-repaired by standard protocols. The end-repaired gC fragment is then cloned into the linearized end-repaired pTK1B as in Example 8. (The cloning can be verified by analysis of the resulting clones with restriction enzymes, probing with radio-actively labelled fragments, or DNA sequencing, or any combination of these).

The resulting plasmid with the RB1B gC gene cloned into the HVT TK gene can then be introduced into the HVT genome by transfecting the plasmid into HVT-infected cells using calcium phosphate precipitation or electroporation. Homologous recombination, involving cross-overs either side of the gC gene, between the HVT virus and the flanking sequences of the HVT TK plasmid will carry the RB1B gC gene into the HVT viral genome. Viral recombinants can be selected for (as they are TK-) or identified (eg by probing) as described above.

In analogous ways, the sequence information given above and in the Figures can be used to design cloning strategies for the insertion of these genes and others into the non-essential genes of the ILTV described here or to generate combinations of antigen genes into ILTV.

We claim:

1. A non-naturally occurring insertional or deletional mutant of ILTV having a mutation in a gene selected from the group consisting of TK, ORF3 and ribonucleotide reductase, large subunit, genes.

2. The mutant of ILTV according to claim 1, wherein a heterologous gene is inserted into a gene selected from the group consisting of TK, ORF3 and ribonucleotide reductase, large subunit, genes.

3. The mutant of ILTV according to claim 1, comprising a mutation in a non-essential site selected from the group consisting of the coding sequences of TK as disclosed in FIG. 7, ORF3 as disclosed in FIG. 7, ribonucleotide reductase, large subunit, gene as disclosed in FIG. 10, and the non-coding sequences thereof.

4. The mutant of ILTV according to claim 2, wherein the heterologous gene codes for an antigen or an antigenic part from HVT, MDV, ILTV, IBV, IBDV, Newcastle Disease, Eimeria, avian encephalomyelitis, avian influenza, avian leukosis, avian paramyxoviruses, avian reovirus diseases, chicken anaemia, coccidiosis, egg drop syndrome, fowl pox, inclusion body hepatitis, lymphoproliferative disease of turkey, reticuloendotheliosis in chickens, reticuloendotheliosis in turkeys, rotavirus enteritis, turkey haemorrhagic enteritis or turkey rhinotracheitis, or paramyosin or an antigenic part thereof, or somatostatin or a growth promoting part thereof.

5. The mutant of ILTV according to claim 2 or 4, wherein the mutant of ILTV further comprises a deletion in the TK, ORF3 or ribonucleotide reductase, large subunit, gene such that the attenuated as a result of said deletion.

6. The mutant of ILTV according to claim 4, wherein the heterologous gene is selected from the group consisting of the gB, gH and IE175 genes of HVT.

7. The mutant of ILTV according to claim 4, wherein the heterologous gene is selected from the group consisting of the gB, gC, gD, IE175 and IE68 genes of MDV.

8. The mutant of ILTV according to claim 7, wherein:

MDV gB gene has the coding portion of the sequence shown in FIGS. 2A to 2R,

MDV gC gene has the coding portion of the sequence shown in FIGS. 6A to 6F,

MDV IE175 gene has the coding portion of the sequence shown in FIG. 15,

MDV IE68 gene has the coding portion of the sequence shown in FIG. 16.

9. The mutant of ILTV according to claim 8, wherein the MDV gB gene is inserted into a site of the ILTV genome which is chosen from the group consisting of the TK, ORF3 and ribonucleotide, large subunit, genes.

10. The mutant of ILTV according to claim 6, wherein:

HVT gB has the coding portion of the sequence shown in FIG. 2,

HVT gH has the coding portion of the sequence shown in FIGS. 4A to 4H,

HVT IE175 has the coding portion of the sequence shown in FIG. 11.

* * * * *